(12) United States Patent
Nie et al.

(10) Patent No.: US 11,678,904 B2
(45) Date of Patent: Jun. 20, 2023

(54) CONTROL END OF SURGICAL INSTRUMENT AND SURGICAL INSTRUMENT HAVING THE CONTROL END

(71) Applicant: EZISURG MEDICAL CO., LTD., Shanghai (CN)

(72) Inventors: Honglin Nie, Shanghai (CN); Jidong Chen, Shanghai (CN); Chuangang Tang, Shanghai (CN); Guang Yang, Shanghai (CN); Menghui Liao, Shanghai (CN); Renmu Tan, Shanghai (CN)

(73) Assignee: EZISURG MEDICAL CO., LTD., Shanghai (CN)

( * ) Notice: Subject to any disclaimer, the term of this patent is extended or adjusted under 35 U.S.C. 154(b) by 265 days.

(21) Appl. No.: 17/017,432

(22) Filed: Sep. 10, 2020

(65) Prior Publication Data
US 2022/0015795 A1    Jan. 20, 2022

Related U.S. Application Data

(60) Provisional application No. 63/052,166, filed on Jul. 15, 2020.

(51) Int. Cl.
*A61B 17/072* (2006.01)
*A61B 17/32* (2006.01)
(Continued)

(52) U.S. Cl.
CPC ......... *A61B 17/320092* (2013.01); *A61B 17/07207* (2013.01); *A61B 17/115* (2013.01); *A61B 2017/00225* (2013.01); *A61B 2017/00398* (2013.01); *A61B 2017/00415* (2013.01); *A61B 2017/00734* (2013.01);
(Continued)

(58) Field of Classification Search
CPC .............. A61B 17/07207; A61B 17/320092
See application file for complete search history.

(56) References Cited

U.S. PATENT DOCUMENTS 9,636,091 B2 * 5/2017 Beardsley .............. A61B 90/70
2008/0269560 A1   10/2008 Ito et al.
(Continued)

FOREIGN PATENT DOCUMENTS

| CN | 104546043 A | 4/2015 |
|----|-------------|--------|
| CN | 105476677 A | 4/2016 |

(Continued)

OTHER PUBLICATIONS

International Search Report of PCT/CN2021/106193 dated Oct. 18, 2021.
(Continued)

*Primary Examiner* — Nathaniel C Chukwurah
(74) *Attorney, Agent, or Firm* — Muncy, Geissler, Olds & Lowe, P.C.

(57) ABSTRACT

The present disclosure discloses a control end of a surgical instrument, which comprises a housing and a power assembly, the housing comprises a first body and a second body, a first cavity for accommodating the power assembly is provided between the first body and the second body, and the power assembly is detachably mounted in the first cavity.

20 Claims, 34 Drawing Sheets

(51) Int. Cl.
*A61B 17/00* (2006.01)
*A61B 17/115* (2006.01)

(52) U.S. Cl.
CPC ............ *A61B 2017/320093* (2017.08); *A61B 2017/320094* (2017.08); *A61B 2017/320097* (2017.08)

(56) References Cited

U.S. PATENT DOCUMENTS

| | | | |
|---|---|---|---|
| 2016/0310134 A1* | 10/2016 | Contini | A61B 17/07207 |
| 2017/0202595 A1* | 7/2017 | Shelton, IV | A61B 18/00 |
| 2017/0325791 A1 | 11/2017 | Fumex et al. | |
| 2018/0206934 A1 | 7/2018 | Healey et al. | |
| 2018/0360460 A1* | 12/2018 | Mozdzierz | A61B 17/3476 |
| 2019/0069887 A1 | 3/2019 | Satti, III et al. | |
| 2019/0069895 A1 | 3/2019 | Satti, III et al. | |
| 2019/0069896 A1 | 3/2019 | Satti, III et al. | |
| 2019/0142423 A1 | 5/2019 | Satti, III et al. | |
| 2019/0175241 A1 | 6/2019 | Hassler, Jr. | |
| 2019/0201025 A1* | 7/2019 | Shelton, IV | A61B 17/072 |
| 2020/0352567 A1 | 11/2020 | Wang et al. | |

FOREIGN PATENT DOCUMENTS

| | | |
|---|---|---|
| CN | 107411793 A | 12/2017 |
| CN | 208524936 U | 2/2019 |
| CN | 208973963 U | 6/2019 |
| CN | 208973964 U | 6/2019 |
| CN | 209899480 U | 1/2020 |
| CN | 110840501 A1 | 2/2020 |
| CN | 109730735 A | 5/2020 |
| CN | 210494159 U | 5/2020 |
| CN | 111281455 A | 6/2020 |
| CN | 111904506 A | 11/2020 |
| EP | 2272446 A2 | 1/2011 |
| WO | WO-2019045995 A1 | 3/2019 |
| WO | WO-2019046132 A1 | 3/2019 |

OTHER PUBLICATIONS

Written Opinion of the international searching authority of PCT/CN2021/106193 dated Oc.t 18, 2021.

* cited by examiner

CONTROL END OF SURGICAL INSTRUMENT AND SURGICAL INSTRUMENT HAVING THE CONTROL END

TECHNICAL FIELD

The present invention relates to the field of surgical instruments, and more particularly to a control end of a surgical instrument and a surgical instrument having the control end.

DESCRIPTION OF THE RELATED ART

At present, there are some electric staplers which can be reused without repeated sterilization in the medical market. Although the cost of using instruments for treatment of patients may be reduced to a certain extent, the core components of the stapler are isolated from the patients only through a physical device when in use, and are simply wiped after use, leading to low sterile control level thereof and thus a cross-infection is easily caused; also, the installation thereof is complex, causing inconvenience for the operation of medical staffs.

SUMMARY

In order to solve the above-mentioned technical problems, the present application provides a control end of a surgical instrument of which core components can be reused, and a surgical instrument having the control end.

The first aspect of the present disclosure is directed to a control end of a surgical instrument wherein the control end comprises a housing and a power assembly, the housing comprises a first body and a second body, a first cavity for accommodating the power assembly is provided between the first body and the second body, and the power assembly is detachably mounted in the first cavity;

the first cavity is closed when the first body and the second body are in a first state; and the first cavity is open when the first body and the second body are in a second state.

In some embodiments, the control end further comprises a transmission assembly, a connector is provided between the power assembly and the transmission assembly, and the power assembly is detachably connected to the transmission assembly in the first cavity so as to drive the transmission assembly to move.

In some embodiments, an input end of the transmission assembly is provided with a fixing hole, and the input end of the transmission assembly is in transmission connection with the connector through the fixing hole; a first resetting spring is provided in the fixing hole, an end of the first resetting spring is abutted against an end of the connector, another end of the first resetting spring is abutted against the fixing hole; and another end of the connector can be in transmission connection with the power assembly. Preferably, the power assembly is located in the first body, and the transmission assembly is located in the second body.

In some embodiments, the transmission assembly comprises a gear set and a screw, or a gear set and a rack, wherein the power assembly is in transmission connection with the gear set via the connector, the gear set is in transmission connection with the screw or the rack, and the power assembly outputs power to the gear set to drive the screw or the rack to move linearly.

In some embodiments, the control end is provided with a rotation mechanism to rotate an end effector, as well as the second body comprises a rotating lock apparatus, through which the rotation mechanism is locked; the screw or the rack is provided with a ganged portion, and the rotating lock apparatus is provided with a firing lock portion, wherein the screw or the rack actuates the rotating lock apparatus through the cooperation of the ganged portion and the firing lock portion to unlock the rotation mechanism.

In some embodiments, the control end further comprises a resetting mechanism actuating the rack or the screw to move.

In some embodiments, the first body is detachably connected to the second body.

In some embodiments, the first body is provided with a snap portion, and the second body is provided with a connection body, wherein the connection body is slidably disposed on the second body, the connection body is provided with a snap connection portion in snap connection with the snap portion, and the snap connection portion is connected to or separated from the snap portion by sliding the connection body.

In some embodiments, both the snap connection portion and the snap portion are provided with guide inclined surfaces, and the first body or the second body is provided with a first opening; wherein, the connection body is actuated to slide by the cooperation of the guide inclined surface of the snap connection portion and the guide inclined surface of the snap portion when the first body and the second body are getting close to each other, such that the snap connection portion enters the first body through the first opening or such that the snap portion enters the second body through the first opening.

In some embodiments, the snap portion comprises a limiting groove disposed in the first body, the snap connection portion is capable of moving along the limiting groove between an engaged position and a disengaged position; wherein the snap portion is in snap connection with the snap connection portion when the snap connection portion is in the engaged position, and wherein the snap portion is disengaged from the snap connection portion each other when the snap connection portion is in the disengaged position.

In some embodiments, the second body is provided with a second resetting spring for driving the snap connection portion to return to the snap connection position when the snap connection portion is located in the limiting groove.

In some embodiments, the limiting groove is provided with a first guide portion, the guide inclined surface of the snap portion is disposed on the first guide portion; the first opening is disposed on the limiting groove, and the first guide portion is disposed at the first opening and partially blocks the first opening; the snap connection portion is provided with a second guide portion matched with the first guide portion, and a guide inclined surface of the snap connection portion is disposed on the second guide portion; wherein, the snap connection portion is driven to slide to the first opening and enter the limiting groove through the first opening via the cooperation of the guide inclined surface of the first guide portion and the guide inclined surface of the second guide portion when the snap connection portion is getting close to the first guide portion along the first direction.

In some embodiments, the control end is provided with a rotation mechanism, and the second body comprises a rotating lock apparatus through which the rotation mechanism is locked to disenable the rotation mechanism to rotate the end effector.

In some embodiments, the rotating lock apparatus is provided with a disassembling lock portion, and the connection body is provided with a disassembling protrusion portion; wherein, the connection body actuates the rotating lock apparatus to unlock the rotation mechanism by the cooperation of the disassembling protrusion portion and the disassembling lock portion.

In some embodiments, the second body is provided with a first actuating mechanism for actuating the connection body.

In some embodiments, the first body is movably connected to the second body such that the first body and the second body are switchable between the first state and the second state.

In some embodiments, the first body comprises a first assembly, a second assembly, and a guide structure, wherein the first assembly and the second assembly cooperate with the guide structure such that the first assembly and the second assembly may be open and closed, wherein the first assembly and the second assembly cooperate with the second body to form the first cavity when the first assembly and the second assembly are closed.

In some embodiments, the guide structure is provided with a first guide groove and a second guide groove, wherein the first assembly is provided with a first buckling portion and is slidably connected to the first guide groove through the first buckling portion, and wherein the second assembly is provided with a second buckling portion and is slidably connected to the second guide groove through the second buckling portion.

In some embodiments, an end of the first buckling portion is slidably connected to the first guide groove, another end of the first buckling portion is hinged to the first assembly; the second buckling portion comprises a second moving end and a second connection bar, an end of the second moving end is hinged to an end of the second connection bar, another end of the second moving end is slidably mounted to the second guide groove, and another end of the second connection bar is hinged to the first assembly.

The second aspect of the present disclosure is directed to a surgical instrument including an end effector and a control end as described in any of the above embodiments, wherein the end effector is detachably connected to the second body.

The advantage of above-mentioned disclosure lies in that, since the power assembly is detachable connected in the first cavity and is separated from the housing, medical staffs is allowed to take out the power assembly of the surgical instruments alone for charging or directly reuse. In addition, because the cost of the power assembly in first cavity is relatively high, the use-cost can be reduced for the user through recycled use multiple times.

BRIEF DESCRIPTION OF THE DRAWINGS

FIG. 35b is a schematic structural view of the snap portion and the snap connection portion corresponding to FIG. 35a.

FIG. 36b is a schematic structural view of the snap portion and the snap connection portion corresponding to FIG. 36a.

Figure 1:
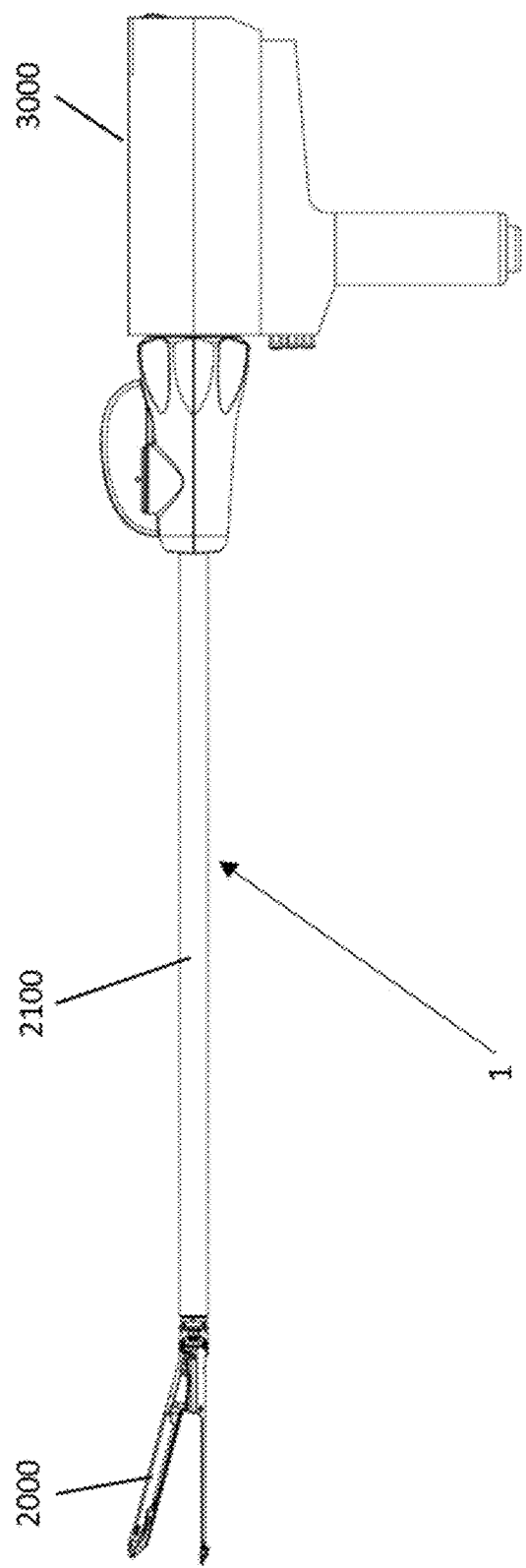
FIG. 1 is a schematic structural view of a surgical instrument according to an exemplary embodiment.

The reference numbers in the drawings: 1: surgical instrument; 2000: end effector; 2100: connection portion; 2200: turning control mechanism; 2210: turning control spanner; 2220: turning control rotating body; 2300: rotating mechanism; 2400: end effector assembly; 3000: control end; 3100: housing; 3600: first cavity; 3110: first body; 3111: first assembly; 3112: second assembly; 3113: guide structure; 3114: first guide body; 31141: first guide groove; 31142: second guide groove; 3115: second guide body; 31151: third guide groove; 31152: guide rack; 3116: second buckling portion; 31161: second moving end; 31162: second connection bar; 31163: fourth rotating shaft; 3117: fourth gear; 3118: second switch member; 3119: first buckling portion; 31191: first moving end; 31192: first connection bar; 31193: third rotating shaft; 3120: second body; 3520: second control key; 3521: button; 3522: signal generator; 3523: sensing element; 3524: keypress spring; 3700: first central processing unit; 3200: power assembly; 3201: drive device; 3202: second housing; 3210: output end of the power assembly; 3220: first fixing structure; 3222: movable member; 3224: first snap groove; 3225: third resetting spring; 3226: seal ring; 3230: power supply; 3235: first convex ring; 3241: protective cover; 3242: third fixing member; 3243: fourth fixing member; 3311: first gear; 3312: second gear; 3313: third gear; 3314: rack; 3321: first bevel gear; 3322: second bevel gear; 3323: screw nut; 3331: first movable gear; 3340: first resetting tool; 3350: second resetting tool; 3351: screw; 2120: screw junction portion; 2130: first connection portion; 3352: first rotating shaft; 3353: second fixing member; 3400: connector (coupling or clutch); 3401: first resetting spring; 3800: first outer shell; 3231: snap portion; 3232: snap connection portion; 3238: connection body; 32381: disassembling protrusion portion; 32382: spring mounting portion; 32383: first lock portion; 32384: guide protrusion; 32385: second resetting spring; 32386: first fixing pillar; 32387: sliding chute; 32388: toggle; 32389: baffle plate; 33111: fixing hole; 32311: limiting groove; 32312: first guide portion; 32313: first opening; 32314: second guide portion; 32315: guide inclined surface; 31201: first actuating mechanism; 31202: cam; 31203: second rotating shaft; 31204: first support; 31205: gland cover; 31206: disassembling toggle; 31207: third rotating shaft; 31211: rotating lock apparatus; 31212: rotating lock portion; 31213: disassembling lock portion; 31214: firing lock portion; 31215: rotating lock spring; 2301: rotating housing; 33511: ganged portion; 33512: nut gear; 33513: screw rotating-stopper; 33514: rotating-stopped groove; 3240: push-button member; 3241: third snap member; 3342: tenth spring; 3250: first snap member; 2302: first groove; 3900: power assembly disassembling mechanism.

DETAILED DESCRIPTION

The present disclosure provides a surgical instrument 1 that can be used to perform laparoscopic and minimally invasive surgical procedures. However, such devices can be used for other surgery and applications, including, for example, open surgery. The surgical instrument 1 may be inserted through a natural orifice or through an incision or puncture formed in the tissue. The operating portion or end effector 2000 of the instrument may be inserted directly into the body or through an access device having an operating channel through which the end effector 2000 and an elongate shaft of the surgical instrument 1 may move forwards. The surgical instrument 1 may be a stapler, ultrasonic knife, electrotome, or another hand-held instrument.

As shown in FIG. 1, in some embodiments, the surgical instrument 1 includes the end effector 2000, a connection portion 2100, and a control end 3000; the control end 3000 is proximal to the connection portion 2100 and the end effector 2000 is distal to the connection portion 2100. The connection of the surgical instrument 1 is achieved by a custom interface. The end effector 2000 is not limited in this disclosure, as the end effector 2000 may be any end effector commercially available or prepared according to the prior art for associated medical apparatus and instruments.

Figure 2:
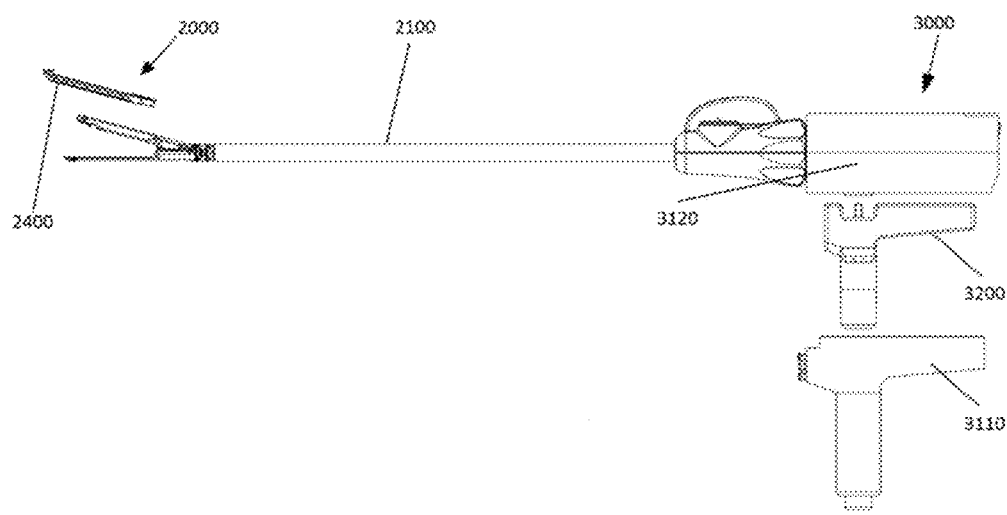
FIG. 2 is an exploded view of some parts of a surgical instrument according to an exemplary embodiment.

As shown in FIG. 2, in some embodiments, the control end 3000 includes a first body 3110, a second body 3120, and a power assembly 3200, the power assembly 3200 transmits power for a desired operation to the end effector 2000 through a clutch 3400, a transmission assembly and the connection portion 2100.

In some embodiments, a first cavity 3600 is formed by the cooperation between the first body 3110 and the second body 3120, and part or all of the transmission assemblies and the power assembly 3200 are disposed in the first cavity 3600. The first cavity 3600 is closed to the outside when the first body 3110 and the second body 3120 are assembled together.

In some embodiments, the first cavity 3600 is closed when the first body 3110 and the second body 3120 are in a first state. It should be appreciated that "the first cavity 3600 is closed" means that the first cavity 3600 which is isolated from the outside but not sealed may be formed, that is, the power assembly 3200 in the first cavity 3600 cannot escape from the first cavity 3600 or a doctor cannot contact the power assembly 3200 through the first cavity 3600. In some embodiments described above, a user cannot contact the power assembly 3200 in the first cavity 3600 because the first cavity 3600 is in a closed state, thus reducing the risk of infection of medical staffs and patients. It should be appreciated that, since the first body 3110 and the second body 3120 are various in structures and assembling manners, the first state of the first body 3110 and the second body 3120 can be varied, which is not specifically limited in this disclosure, while some specific structures will be described in the following embodiments. In some embodiments, when the first body 3110 and the second body 3120 are in the first state, the first body 3110 and the second body 3120 are engaged with each other, optionally, the first body 3110 is connected to the second body 3120.

In some embodiments, the first cavity 3600 is in a sealed state when the first body 3110 and the second body 3120 are in the first state. "The sealed state" means that first cavity 3600 is completely sealed to form a microorganism barrier, and not only power assembly 3200 cannot escape from first cavity 3600, but also microorganisms such as bacteria cannot escape from first cavity 3600. As the first cavity 3600 is in the sealed state, it further reduces the contamination to the power assembly 3200 and avoids a contaminated power assembly 3200 infecting tissues during use in the operation.

In some embodiments, when the first body 3110 and the second body 3120 are in the second state, the first cavity 3600 is in an open state. "The open state" means that the first body 3110 is partially or fully separated from the second body 3120 such that the power assembly 3200 can be removed from the first cavity 3600. Since the first body 3110 and the second body 3120 can be engaged in various manners, the second state can be varied in different engaging manners, for example, in some embodiments, the first body 3110 and the second body 3120 are separated from each other when the first body 3110 and the second body 3120 are in the second state, and some specific structures will be described in the following embodiments.

In some embodiments, the first cavity 3600 is located in first body 3110 and the second body 3120 is simply capped over the first body 3110 for sealing the first cavity 3600, in the meanwhile, the power assembly 3200 may be fully entered the first body 3110 through the first cavity 3600.

In some embodiments, the power assembly 3200 is used to drive the movement of the transmission assembly, and the power assembly 3200 is detachably connected to the transmission assembly in the first cavity 3600 to drive the movement of the transmission assembly.

In some embodiments, the first body 3110 is located below the second body 3120, as shown in FIG. 2. The control end 3000 includes a structure that enables the manipulation of the end effector 2000 to accomplish a desired operation on the tissue. In some embodiments, the end effector 2000 includes an end effector assembly 2400 which includes a staple cartridge, a slider, a pushing staple, and titanium staples; through driving the motion of the slider, the slider pushes the pushing staple to move in the inner hole of the staple cartridge, and the pushing staple pushes the titanium staples to move so as to realize the desired action on the biological tissues. The slider pushes the pushing staple to push the anastomotic staple out from the staple cartridge to penetrate the clamped anastomotic tissue to be cut and directly abut against an anastomotic staple shaping groove on a staple anvil, such that the anastomotic staple of a U-shape is bent into a B shape, achieving the purpose of the operation of anastomosing the tissue. Since the forms of the end effector 2000 may be various, the present disclosure is not particularly limited.

In some embodiments, the second body 3120 includes a transmission assembly having a connection structure that is connected to the connection portion 2100, and a partial connection structure that is partially connected to the power assembly 3200. The connection portion 2100 is primarily used to connect the output of the control end 3000 to the input end of the end effector 2000 in transmission manner to control the end effector 2000 to perform a desired action.

In some embodiments, the first body 3110 is connected to the second body 3120 by a snap structure, and the first body 3110 and the second body 3120 are in the first state when the snap structure is in a connected state.

In some embodiments, the first body 3110 is movably connected to the second body 3120 such that the first body 3110 and the second body 3120 can be switched between the first state and the second state.

In some embodiments, the connection of the first body 3110 and the second body 3120 is achieved by longitudinal movement of the first body 3110 and the second body 3120.

It should be appreciated that in some embodiments, the first body 3110 is detachably connected to the second body 3120. In some embodiments, the snap structure includes a connection body 3238 and a snap portion 3231, the connection body 3238 is disposed on the second body 3120, the snap portion 3231 is disposed on the first body 3110, and the connection body 3238 is detachably connected to the snap portion 3231, as shown in FIG. 12-14, FIG. 15a and FIG. 15b. The snap portion 3231 of the first body 3110 is connected to a snap connection portion 3232 of the connection body 3238 when the first body 3110 is mounted to the second body 3120.

More specifically, in some embodiments, the connection body 3238 is further provided with a disassembling protrusion portion 32381, a spring mounting portion 32382, a first lock portion 32383, and a guide protrusion 32384, wherein the number of the snap connection portions 3232 is not limited to 4 as long as it is not less than 1. In some embodiments, the guide protrusion 32384 is slidably connected to the second body 3120 such that the connection body 3238 moves in one direction.

Figure 15A:
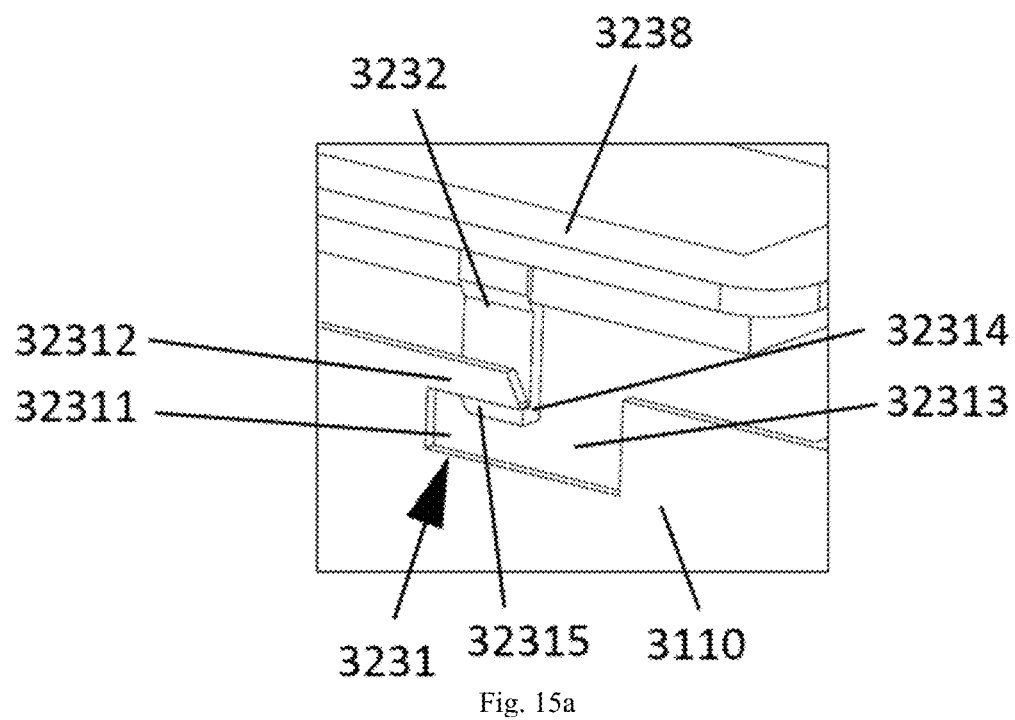
FIG. 15a is a schematic structural view of a snap connection portion and a snap portion being connected according to an exemplary embodiment.
Figure 15B:
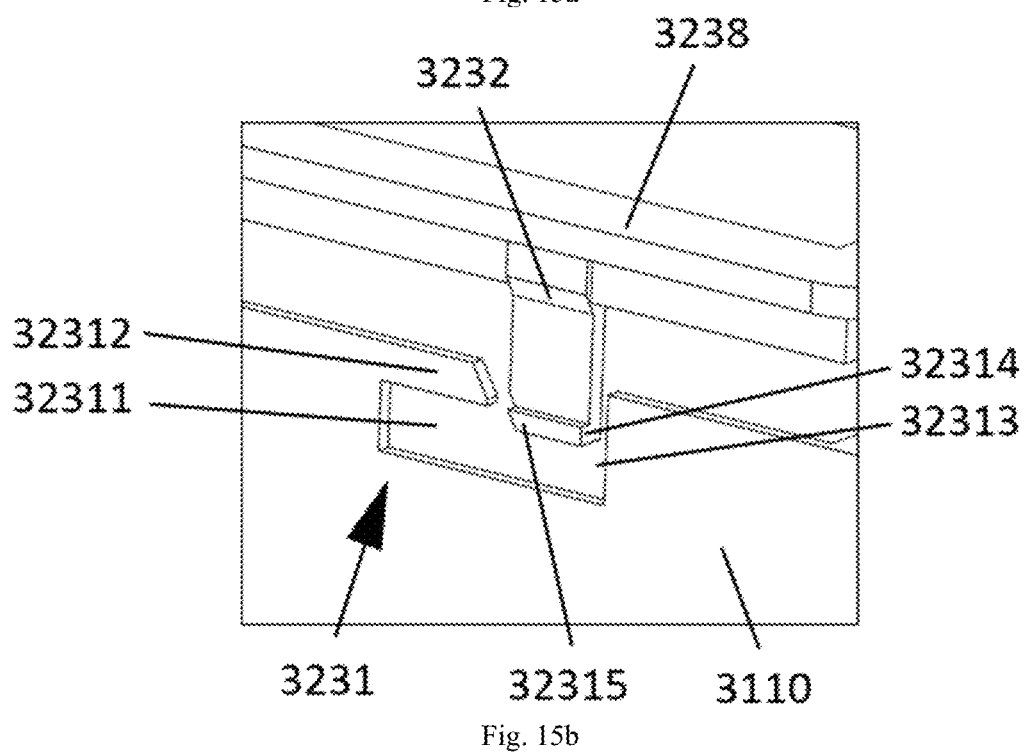
FIG. 15b is a schematic structural view of a snap connection portion and a snap portion ready to be connected according to an exemplary embodiment.

In some embodiments, a second resetting spring 32385 is mounted at a proximal end of the connection body 3238, and more particularly, the second resetting spring 32385 is mounted to the connection body 3238 by a spring mounting portion 32382. The connection body 3238 can move in an extending direction of the guide protrusion 32384 (i.e., a direction the same as or opposite from the proximal end toward the distal end) by the second resetting spring 32385. When the first body 3110 is mounted to the second body 3120, the snap portion 3231 of the first body 3110 and the snap connection portion 3232 of the connection body 3238 abut against each other such that the connection body 3238 moves to the proximal end until the snap connection portion 3232 aligns with a notch of the snap portion 3231 of the first body 3110, as shown in FIG. 15b. In the meanwhile, the connection body 3238 moves to the distal end by the second resetting spring 32385 to achieve the mutual engagement of the connection body 3238 and the first body 3110. FIG. 15a is a schematic structural view of the snap connection portion 3232 and the snap portion 3231 being connected, in the meanwhile, the connection body 3238 within the second body 3120 is locked with the first body 3110 so as to complete the assembly of the surgical instrument 1, and in the meanwhile, the first body 3110 and the second body 3120 are in the first state.

The snap portion 3231 includes a limiting groove 32311 disposed in the first body 3110, the snap connection portion 3232 can move along the limiting groove 32311 between an engaged position and a disengaged position. The snap portion 3231 are in snap connection with the snap connection portion 3232 when the snap connection portion 3232 is in the engaged position, and the snap portion 3231 and the snap connection portion 3232 are separated from each other when the snap connection portion 3232 is in the disengaged position.

Figure 16A:
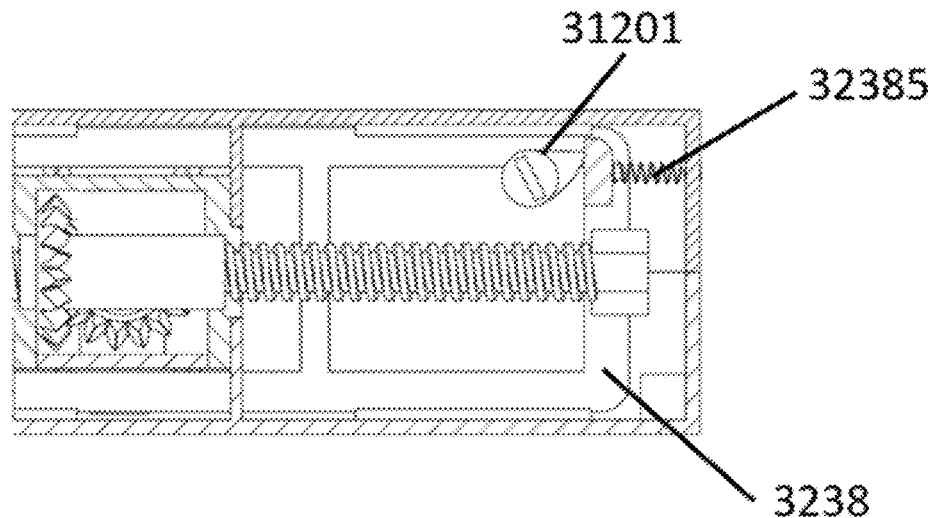
FIG. 16a is a schematic view of an internal structure of a second body (with a second resetting spring being compressed) according to an exemplary embodiment.
Figure 16B:
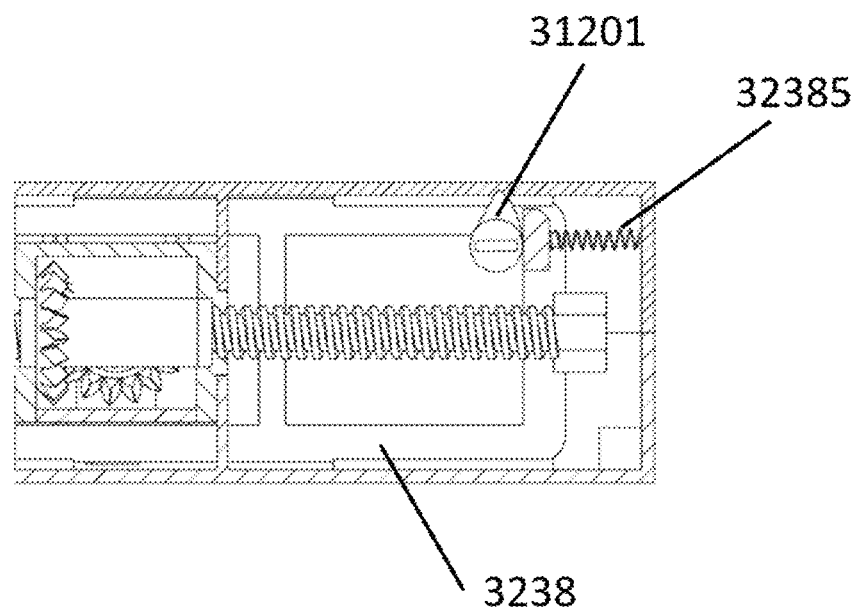
FIG. 16b is a schematic view of an internal structure of a second body (with a second resetting spring being released) according to an exemplary embodiment.

In some embodiments, the snap portion 3231 includes a limiting groove 32311 disposed on the first body 3110 and a first guide portion 32312, the limiting groove 32311 is provided with a first opening 32313, and the first guide portion 32312 is disposed at the first opening 32313 and partially blocks the first opening 32313. Meanwhile, the snap connection portion 3232 is provided with a second guide portion 32314 which is matched with the first guide portion 32312, and when the first body 3110 is mounted to the second body 3120, the first guide portion 32312 and the second guide portion 32314 abut against each other, such that the connection body 3238 moves toward the proximal end and enters the limiting groove 32311 through the first opening 32313, and in the meanwhile, the snap connection portion 3232 is in the disengaged position. Next, the connection body 3238 is moved toward the distal end by the second resetting spring 32385, such that the second guide portion 32314 is positioned in the limiting groove 32311 and below the first guide portion 32312, thereby realizing the mutual engagement of the connection body 3238 with the first body 3110. As shown in FIG. 16b, in the meanwhile the connection body 3238 in the second body 3120 is locked with the first body 3110, completing the assembly of the surgical instrument 1, and in the meanwhile the first body 3110 and the second body 3120 are also in the first state. It should be appreciated that, in some embodiments, a matched guide inclined surface 32315 is disposed between the first guide portion 32312 and the second guide portion 32314, and when the second guide portion 32314 abuts against the first guide portion 32312 from top to bottom through the guide inclined surface 32315, the second guide portion 32314 moves towards the notch of the first opening 32313 under the guidance of the guide inclined surface 32315, and enters the limiting groove 32311. It should be appreciated that the second body 3120 is provided with a first actuating mechanism 31201 such that the user may use the first actuating mechanism 31201 within the second body to actuate the connection body 3238. The specific structure of the first actuating mechanism 31201 will be described below in the specification.

In some embodiments, the snap connection portion 3232 is provided with a second guide portion 32314 matched with the first guide portion 32312, such that when the snap connection portion 3232 approaches the first guide portion 32312 in the first direction, the snap connection portion 3232 is driven by the cooperation of the first guide portion 32312 and the second guide portion 32314 to slide into the first opening 32313 and into the limiting groove 32311 through the first opening 32313.

In some embodiments, the extending direction of the limiting groove 32311 is the same as the sliding direction of the connection body 3238 and is the same direction or the opposite direction from the proximal end to the distal end, and the first direction is perpendicular to the sliding direction of the connection body 3238.

In some embodiments, in an assembled surgical instrument 1, the transmission assembly is configured to convert the power output of power assembly 3200 into an action associated with the actuator; in particular, the transmission assembly converts the rotational motion output by power assembly 3200 into a linear motion, leading to changing the configuration of end effector 2000 so as to perform a desired operation. In more detail, the configuration changes of the end effector 2000 include for example closed and open states.

It should be appreciated that the connection manner of the first body 3110 and the second body 3120 is various; in addition to the above connection manner, the first body 3110 and the second body 3120 may also use other snap connection manners and latch connection manners.

It should be appreciated that the above connection manner is not limited to the connection of the first body 3110 and the second body 3120, and the power assembly 3200 may be connected to the second body 3120 in the same connection manner.

Figure 3:
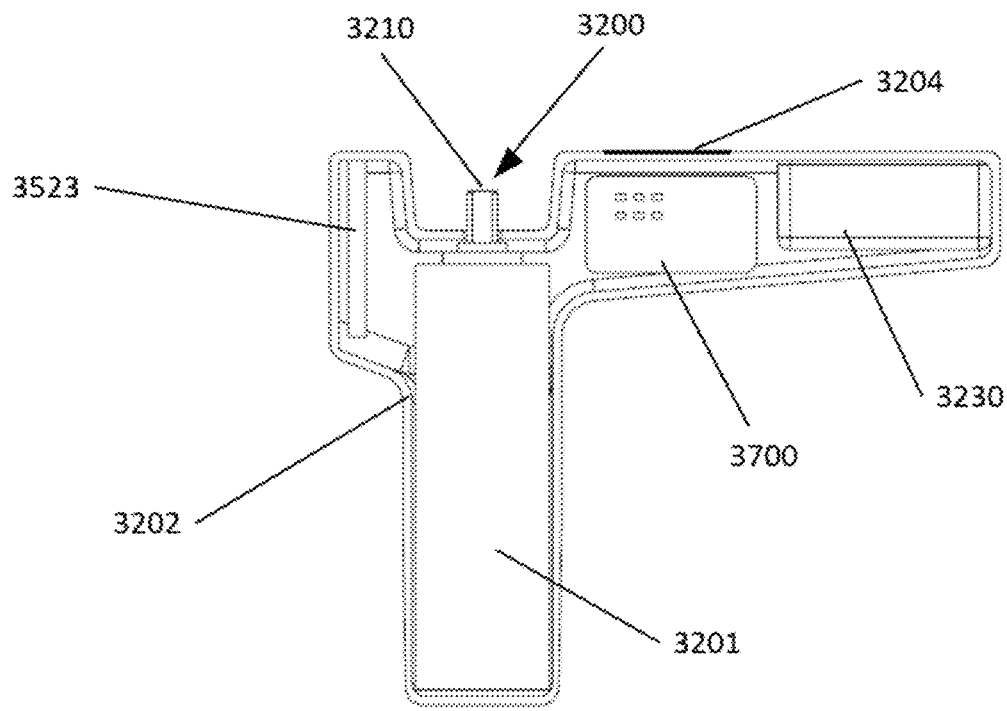
FIG. 3 is a schematic structural view of a power assembly according to an exemplary embodiment.

As shown in FIG. 3, the power assembly 3200 is provided with an outwards output shaft (i.e. the output end 3210 of the power assembly), and the output shaft of the power assembly 3200 outputs a rotational motion. In some embodiments, the power assembly 3200 includes a second housing 3202, a drive device 3201, a power supply 3230, a first central processing unit 3700, a second central processing unit 3203. As a reusable component, the second housing 3202 forms one or more cavities, of which one or more are sealed. In some embodiments, the power assembly 3200 may further include a signal display device 3204 to identify detected information of the power assembly 3200, or generated or received by the power assembly 3200. The signal display device 3204 may be an LED lamp (group) or a display screen. FIG. 3 illustrates certain features of the power assembly 3200, and it should be recognized that certain features are optional and may be modified as desired.

In some embodiments, an input end of the transmission assembly is provided with a fixing hole, and the input end of the transmission assembly is in transmission connection with the connector-through the fixing hole; a first resetting spring is disposed in the fixing hole, an end of the first resetting spring is abutted against an end of the connector, another end of the first resetting spring is abutted against the fixing hole; and another end of the connector can be in transmission connection with the power assembly. Optionally, the power assembly is located in the first body and the transmission assembly is located in the second body.

In some embodiments, the power assembly 3200 is mounted within the first body 3110. To better understand how the output of the power assembly 3200 is transmitted to the end effector 2000, firstly referring to FIGS. 7 to 11, a coupling 3400 is disposed in a first bevel gear 3321, the first bevel gear 3321 is provided with the fixing hole 33111 therein, and the coupling 3400 is of a shape matched the fixing hole 33111 and can move along the fixing hole 33111 under the action of the first resetting spring 3401. In some embodiments, the first body 3110 and the second body 3120 approach towards and are connected in a first direction, and the fixing holes 33111 extend in the same direction or in an opposite direction to the first direction.

Figure 11A:
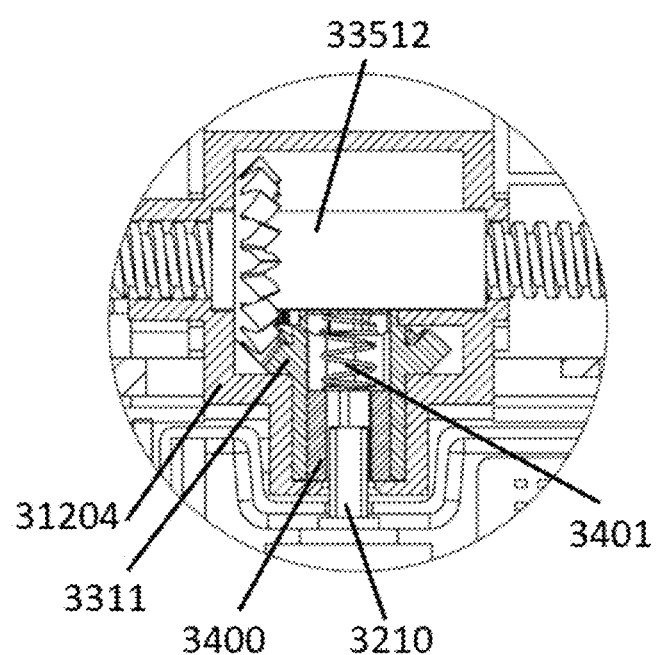
FIG. 11a is a schematic structural view of a first body and a second body being connected (with a coupling and an output shaft of a power assembly mounted together) according to an exemplary embodiment.
Figure 11B:
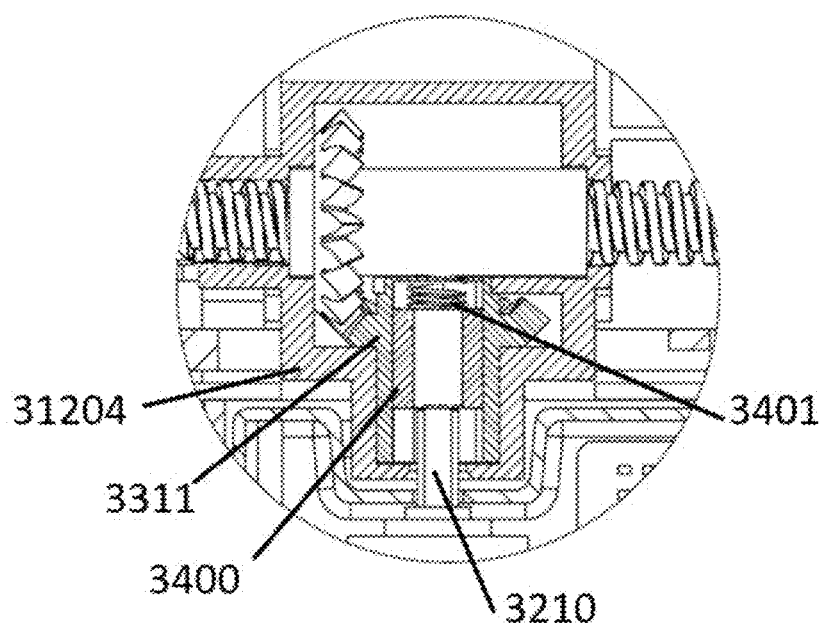
FIG. 11b is a schematic structural view of a first body and a second body when being connected (with a coupling and an output shaft of a power assembly not yet properly mounted) according to an exemplary embodiment.
Figure 11C:
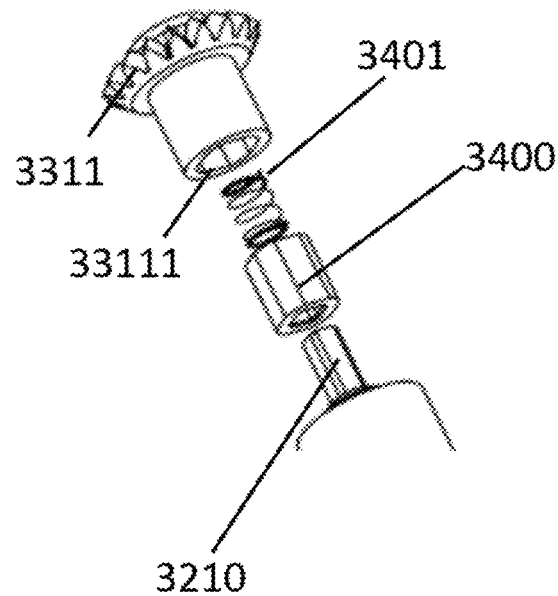
FIG. 11c is a schematic structural view of a coupling and a first gear according to an exemplary embodiment.
Figure 12:
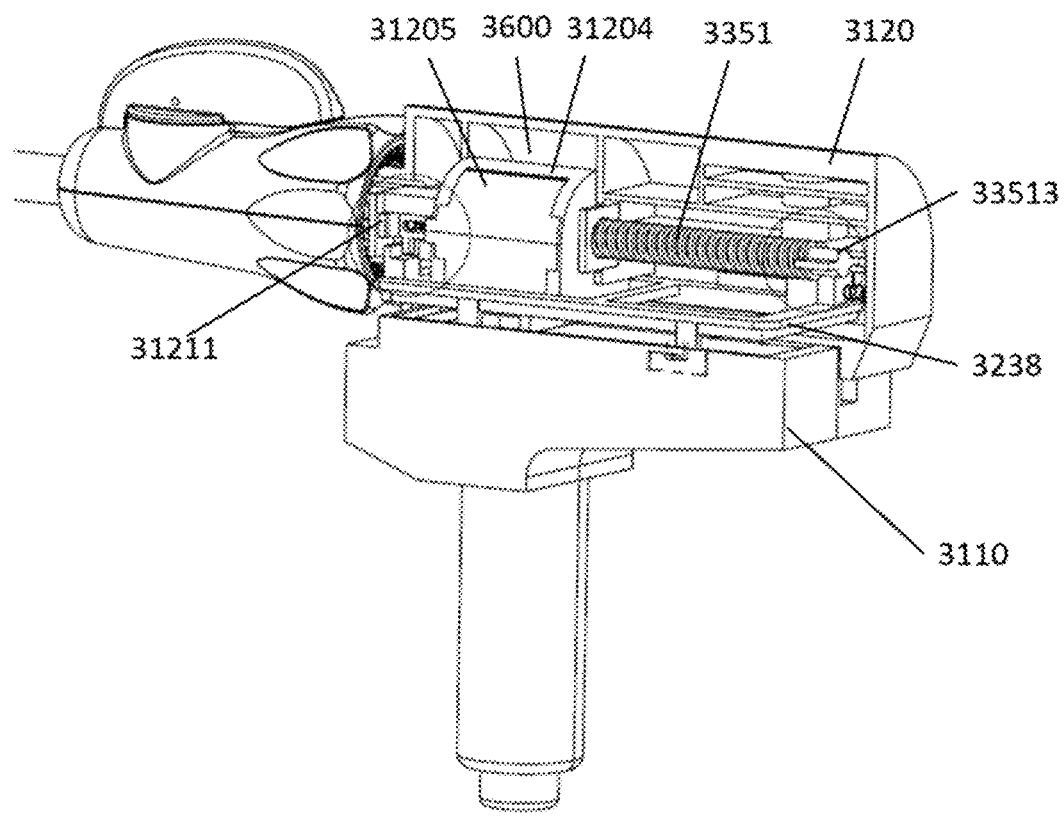
FIG. 12 is a schematic view of an internal structure of a second body according to an exemplary embodiment.

FIG. 11c shows the relationship between the power assembly output end 3210, the coupling 3400 and the first bevel gear 3321. The power assembly output end 3210 is coaxially arranged with the coupling 3400; the cross-section of the power assembly output end 3210 is non-circular, preferably polygonal; and the inner hole of the coupling 3400 is matched with the shape of the power assembly output end 3210.

When the first body 3110 is connected to the second body 3120, the power assembly output end 3210 is docked with the coupling 3400, and there are two possible dock states:

The first dock state: when the output shaft of the power assembly 3200 (i.e. the power assembly output end 3210) engages with the coupling 3400 on four sides as shown in FIG. 11c, the output shaft of the power assembly 3200 can be completely inserted into a coupling hole, as shown in FIG. 11a. In addition, the connecting feature between the external shape of the protrusion portion of the coupling 3400 and the first bevel gear 3321, as well as the connecting feature between the coupling 3400 and the output shaft of the power assembly 3200, are not limited to the square-shape hole shown in FIG. 11c, and a triangular-shape hole, a pentagonal-shape hole, or a polygonal hole may be used. The second dock state: when the output shaft of the power assembly 3200 is not engaged with the coupling 3400, the coupling 3400 floats upwards and compresses a first coupling spring 3401, as shown in FIG. 11b. Meanwhile, after the output shaft of the power assembly 3200 or the coupling 3400 rotates by a certain angle, when the output shaft of the power assembly 3200 is engaged with the coupling hole, the coupling 3400 moves downwards to be reset under the action of the coupling spring 3401 to achieve the engagement with the output shaft of the power assembly 3200, and then the output of the power assembly 3200 is transmitted to the first bevel gear 3321 through the coupling 3400. In some embodiments, the power assembly 3200 may be in transmission connection with the transmission assembly without the coupling 3400, and the power assembly 3200 may be in transmission connection directly with the transmission assembly.

Figure 10A:
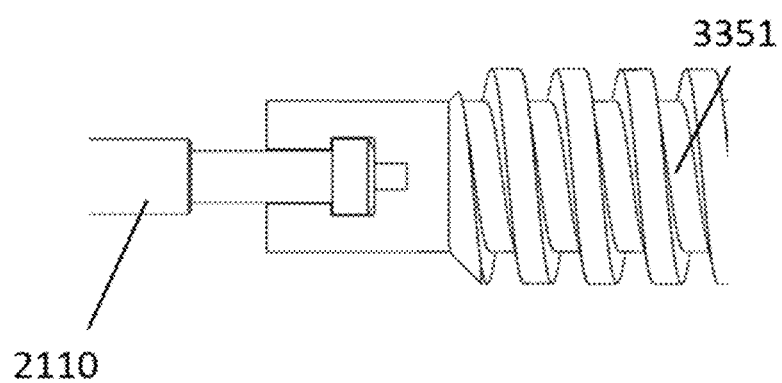
FIG. 10a is a schematic structural view of a connection rod and a screw being connected according to an exemplary embodiment.
Figure 10B:
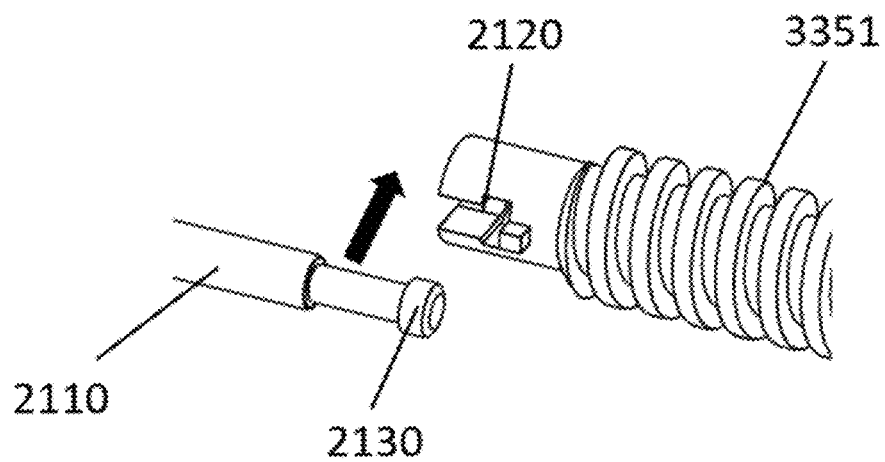
FIG. 10b is a schematic structural view of a connection rod and a screw being separated according to an exemplary embodiment.
Figure 13A:
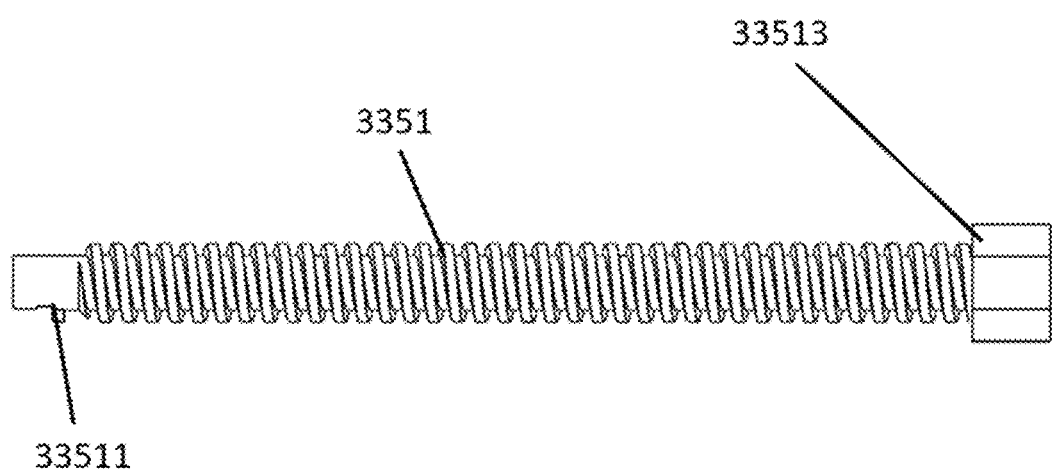
FIG. 13a is a schematic structural view of a screw according to an exemplary embodiment.
Figure 13B:
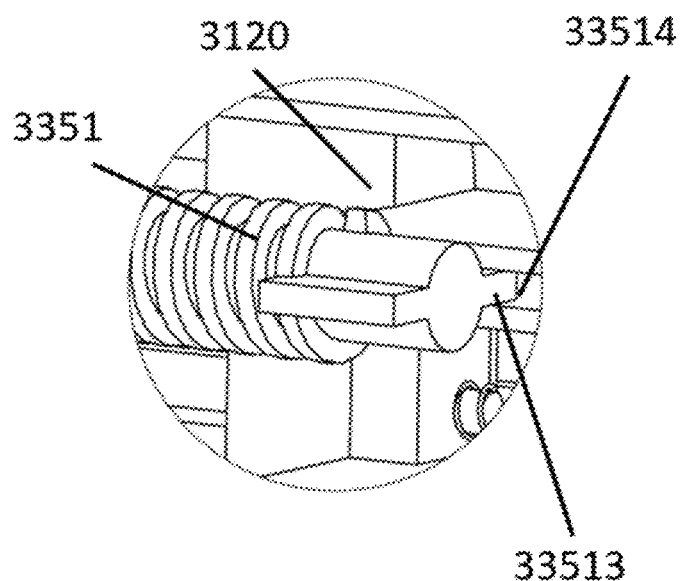
FIG. 13b is a partial schematic view of a screw mounted in a second body according to an exemplary embodiment.
Figure 14:
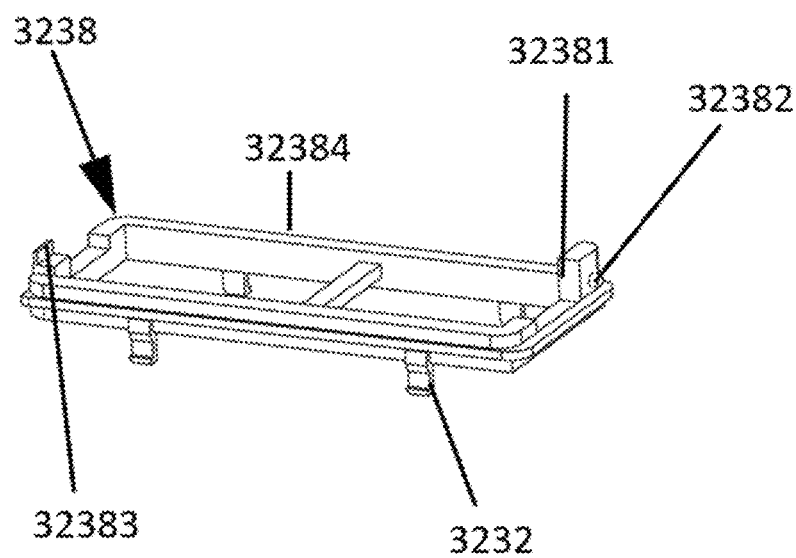
FIG. 14 is a schematic structural view of a connection body according to an exemplary embodiment.

In some embodiments, the transmission assembly includes a gear se and a screw, the power assembly is in transmission connection with the gear set, and the gear set is in transmission connection with the screw. More specifically, with further reference to FIGS. 7 and 8, the transmission assembly includes a first bevel gear 3321, a nut gear 33512, and a screw 3351, and a first support 31204 is provided in the second body 3120 for limiting the degrees of freedom of the first bevel gear 3321, the nut gear 33512, and the screw 3351 mentioned above. In the inner cavity of the control end 3000, a motor drives the first bevel gear 3321 to move through the coupling 3400, the first bevel gear 3321 is meshed with the nut gear 33512, the first bevel gear 3321 and the nut gear 33512 are both mounted on the first support 31204 and are fixedly mounted through a gland cover 31205 connected to the first support 31204, and the first support 31204 is fixed on the second body 3120; through the arrangement mode of the gears, the rotation of the first bevel gear 3321 drives the nut gear 33512 to rotate, and the rotation axis of the first bevel gear 3321 is not parallel to that of the nut gear 33512 in space; the rotation of the nut gear 33512 further drives the screw 3351 to do linear motion; the screw 3351 is provided with a screw rotating-stopper 33513 (as shown in FIG. 13), the second body is provided with a rotating-stopped groove 33514 matched with the screw rotating-stopper, and the rotation of the screw 3351 is prevented by the matching of the rotating-stopped groove 33514 and the screw rotating-stopper 33513; the screw 3351 is connected to the connection rod 2110 of the connection portion 2100, the connecting structure is as shown in FIGS. 10a and 10b, the screw 3351 is provided with a screw junction portion 2120, the connection rod 2110 is provided with a first connection portion 2130, the screw 3351 is connected to the connection rod 2110 by assembling the screw junction portion 2120 and the first connection portion 2130, and the desired action of the end effector 2000 is further controlled by the connection rod 2110. The transmission assembly allows the user to operate the desired action by actuating the first bevel gear 3321 to drive the connection rod 2110 and the end effector 2000. Accordingly, the power assembly 3200 can be in transmission connection with the end effector 2000 via the coupling 3400, the transmission assembly, or the like, so as to realize control of the end effector 2000. It should be appreciated that the gear set can be other gear transmission structures besides the first bevel gear 3321 and the nut gear 33512 as in the above embodiments, and the disclosure is not limited in particular.

Figure 9:
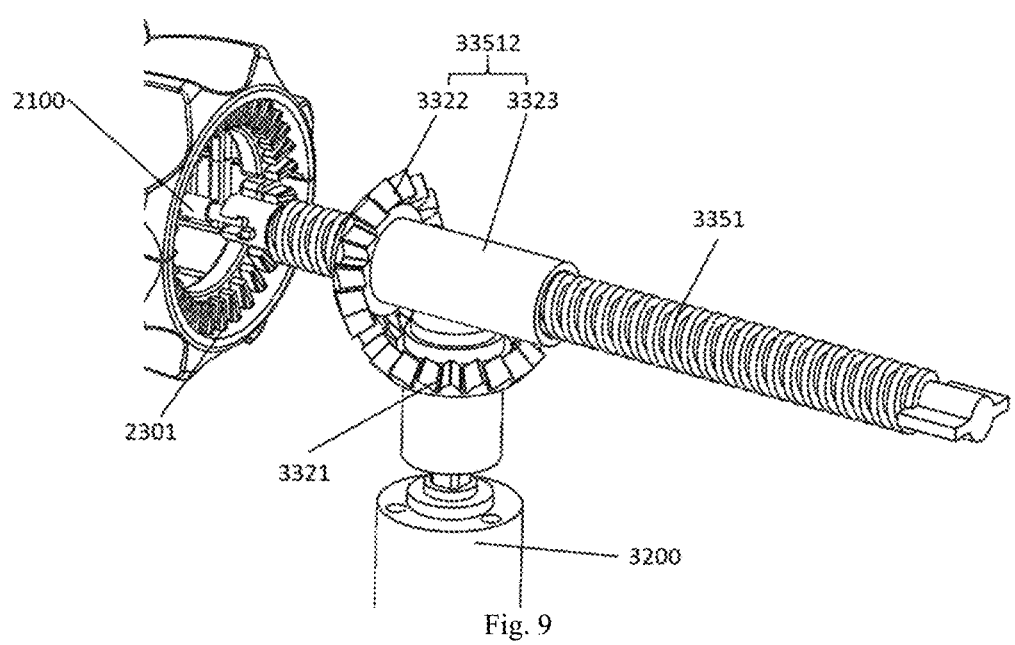
FIG. 9 is a schematic view of an assembly structure of a power assembly, a coupling, a transmission assembly and a connection portion according to an exemplary embodiment.

As further clearly illustrated in FIG. 9 how the rotational motion of power assembly 3200 is converted into linear motion of connection rod 2110. The transmission assembly includes the first bevel gear 3321, the nut gear 33512 and the screw 3351, the first bevel gear 3321 is fixed at one end of the clutch 3400 or the coupling 3400, or at the power assembly output end 3210 (in the embodiment without the coupling 3400 or the clutch 3400), and the nut gear 33512 is in transmission connection with the first bevel gear 3321. In some embodiments, the nut gear 33512 is provided with a second bevel gear 3322 and a screw nut 3323, the second bevel gear 3322 is meshed with the first bevel gear 3321, the screw nut 3323 is meshed with the screw 3351, and the distal end of the screw 3351 is connected to the connection rod 2110. To better illustrate how the transmission assembly described above achieves transmission, this disclosure provides some examples, for example, the power assembly output end 3210 may rotate counterclockwise, and transmit torque through the dock coupling with the clutch 3400; the clutch 3400 drives the first bevel gear 3321 to rotate counterclockwise, the first bevel gear 3321 is meshed with the second bevel gear 3322, and the second bevel gear 3322 rotates clockwise after reversing; the second bevel gear 3322 is fixed to the screw nut 3323, the screw nut 3323 is coupled with the screw 3351, the screw 3351 is connected to the output end of the transmission assembly, the rotation of the screw 3351 is restricted by the second body 3120; the screw nut 3323 rotates clockwise, the screw 3351 moves towards the distal end, and the movement of the end effector 2000 is controlled by the connection rod 2110. Conversely, the motor output shaft rotates clockwise, and by means of above transmissions, the connection rod 2110 is driven to move towards the proximal end. In the above solution, the first bevel gear 3321, the second bevel gear 3322, the screw 3351 and the screw nut 3323 are arranged in the center, and the rotating motion of the power assembly 3200 is converted into linear motion through the arrangement of the first bevel gear 3321, the second bevel gear 3322, the screw nut 3323 and the screw 3351, such that large-amplitude transmission is realized in a small space, the torque of the motor is effectively expanded by different orders of magnitude, thus reducing the requirement on the torque of the motor, i.e. a small-torque motor can satisfy the output of large thrust.

Figure 6:
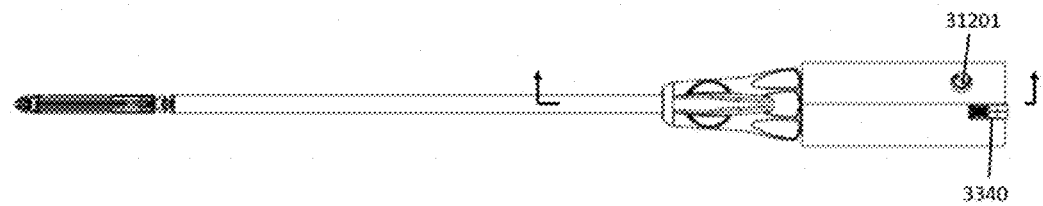
FIG. 6 is a schematic structural view of a surgical instrument according to an exemplary embodiment.
Figure 7:
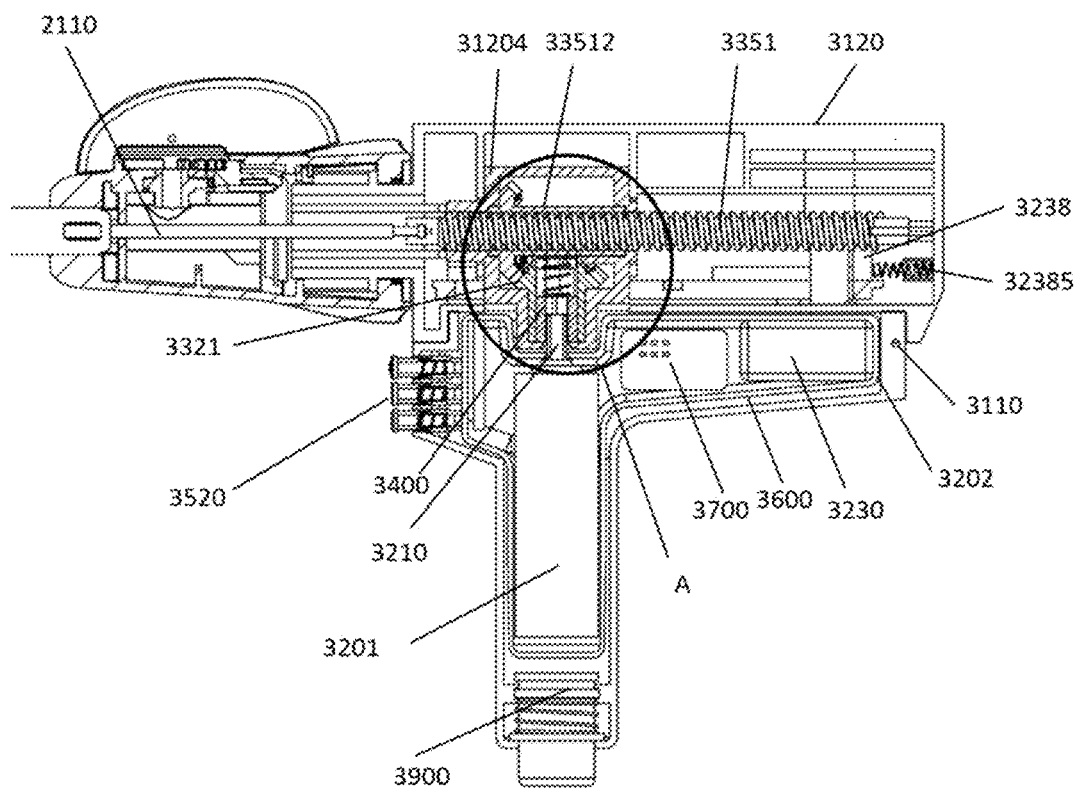
FIG. 7 is a schematic view of an internal structure of a control end according to an exemplary embodiment.
Figure 8:
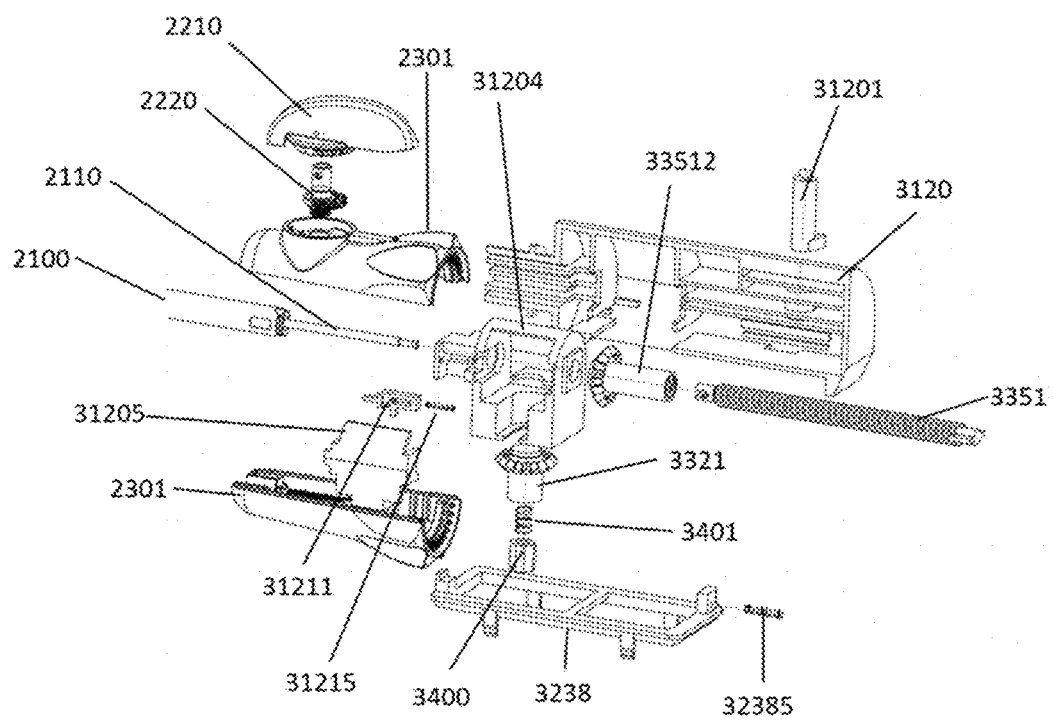
FIG. 8 is an exploded view of a control end according to an exemplary embodiment.
Figure 20:
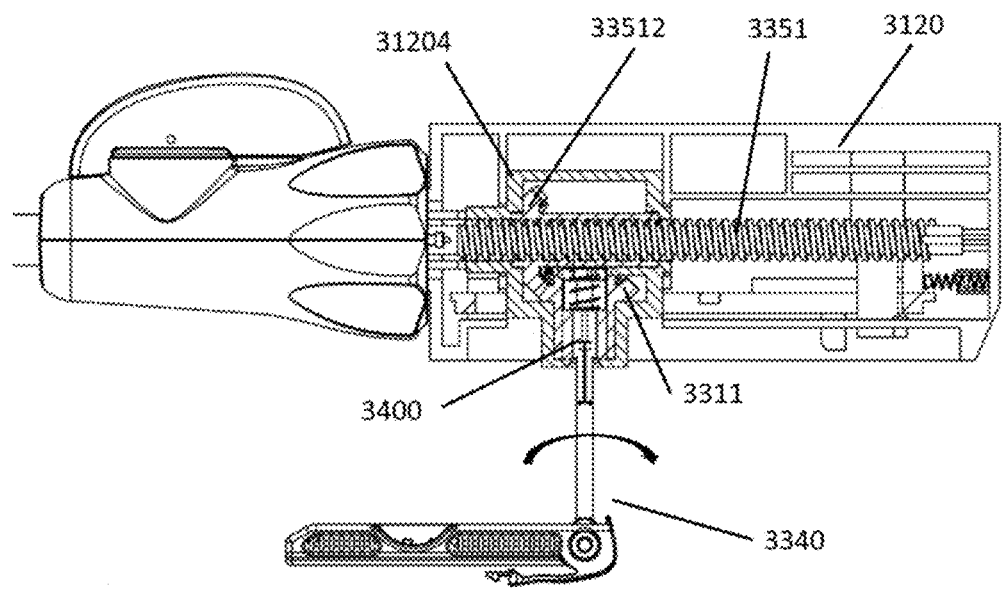
FIG. 20 is a schematic structural view of a first resetting tool during use according to an exemplary embodiment.

In some embodiments, as shown in FIG. 6, the first resetting mechanisms may include a first resetting tool 3340 and/or a second resetting tool 3350, and the second body 3120 is provided with a first reset tool 3340. The connection between the first body 3110 and the second body 3120 can be released when a first actuating mechanism 31201 is operated, as shown in FIGS. 15a and 15b, in the meanwhile, the first body 3110 and the power assembly 3200 can be removed, and the first resetting tool 3340 can be taken out of the second body 3120 and then inserted into the coupling 3400, as shown in FIG. 20. The screw 3351 can be driven to move linearly by manually rotating the first resetting tool 3340, thereby realizing the manual operation of the surgical instrument 1.

Figure 24:
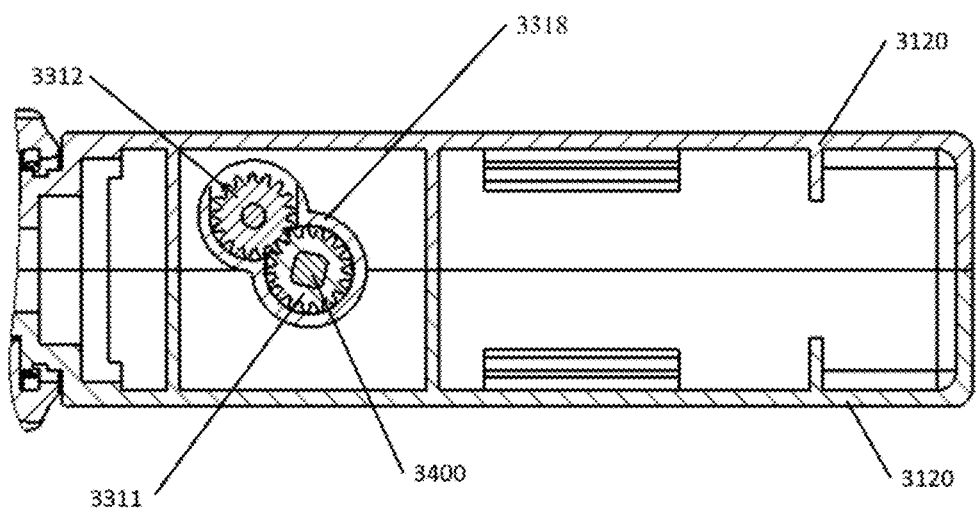
FIG. 24 is a schematic structural view of cross-section C according to an exemplary embodiment.
Figure 25:
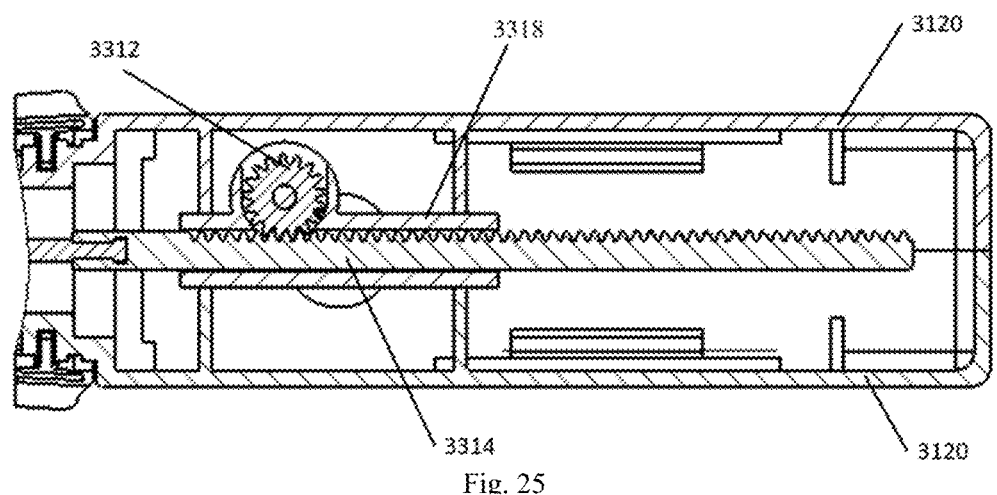
FIG. 25 is a schematic structural view of cross-section D according to an exemplary embodiment.

It should also be appreciated that the specific construction of the transmission assembly is widely varied, as in some embodiments the surgical instrument has different transmission assembly configurations, as shown particularly in FIGS. 24-26.

To better illustrate the cooperation of the transmission assembly with the power assembly 3200, FIGS. 24 and 25 therefore illustrate cross-sectional views of the surgical instrument 1 in different positions. In the embodiment described above, the power assembly 3200 has a generally centered drive shaft that outputs rotational motion, and the coupling 3400 is disposed coaxially with the drive shaft.

In some embodiments, as shown in FIGS. 24-26, the transmission assembly includes a first gear 3311 coaxially disposed with respect to the coupling 3400, and an eccentrically disposed second gear 3312 meshed with the first gear 3311, wherein the second gear 3312 is meshed with a rack 3314. The second body 3120 is further provided with a gear frame 3318 disposed therein, which covers the periphery of the coupling 3400, thus the coupling 3400 can move only along a predetermined track under the guidance of the gear frame 3318. The gear frame 3318 further restricts the degrees of freedom of the first gear 3311, the second gear 3312, and the rack 3314.

Figure 46:
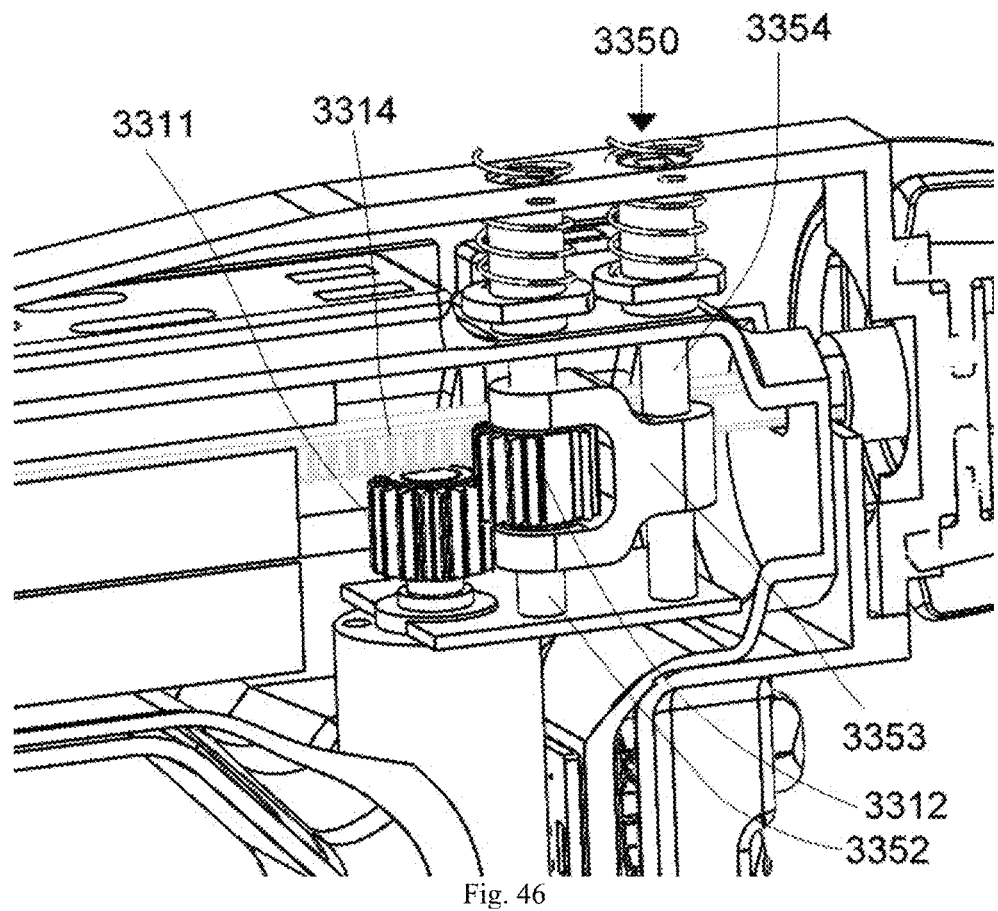
FIG. 46 is a schematic view of a second resetting tool during use according to an exemplary embodiment.
Figure 47:
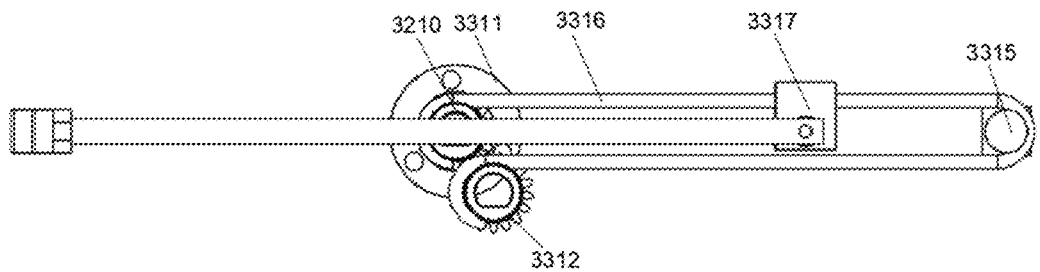
FIG. 47 is a schematic structural view of a transmission assembly according to an exemplary embodiment.

Meanwhile, in some embodiments, as shown in FIG. 46, the transmission assembly further includes a second resetting tool 3350, the second resetting tool 3350 includes a first threaded rod 3354, a first rotating shaft 3352, and a second fixing member 3353, wherein the second fixing member 3353 is provided with a threaded hole matched with the first threaded rod 3354, and a fixing groove for placing the second gear 3312. The first rotating shaft 3352 passes through the second fixing member 3353 and is coaxial with the second gear 3312. In some embodiments, the first threaded rod 3354 is provided with a first knob located outside of the housing 3100, and the first rotating shaft 3352 is provided with a second knob located outside of housing 3100. When the rack 3314 needs to be reset, the first resetting tool 3340 is inserted into the first knob to rotate the first knob and drive the first threaded rod 3354 to rotate, and then the second fixing member 3353 in turn is driven to move along the first threaded rod 3354, such that the second gear 3312 placed in the fixing groove also moves along with the first knob, and the first gear 3311 is disengaged from the second gear 3312, and then the first resetting tool 3340 is inserted into the second knob to rotate the second knob and drive the first rotating shaft 3352 to rotate, and the second gear 3312 is driven to rotate, such that the second gear 3312 drives the rack 3314 to move, thereby realizing the reset of the rack 3314. Upon the rack 3314 is reset, the first resetting tool 3340 is repeatedly used to rotate the first knob, so as to drive the first threaded rod 3354 to rotate, and further drive the second fixing member 3353 to move, such that the first gear 3311 is in transmission connection with the second gear 3312 again.

Figure 26A:
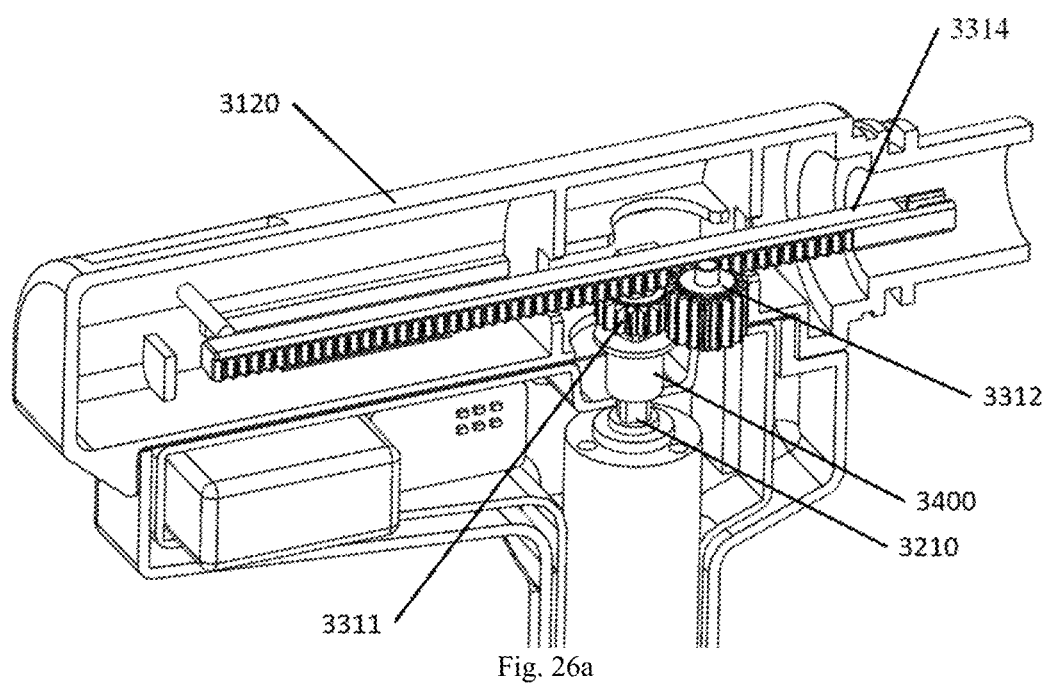
FIG. 26a is a cross-sectional view of a control end according to an exemplary embodiment.
Figure 26B:
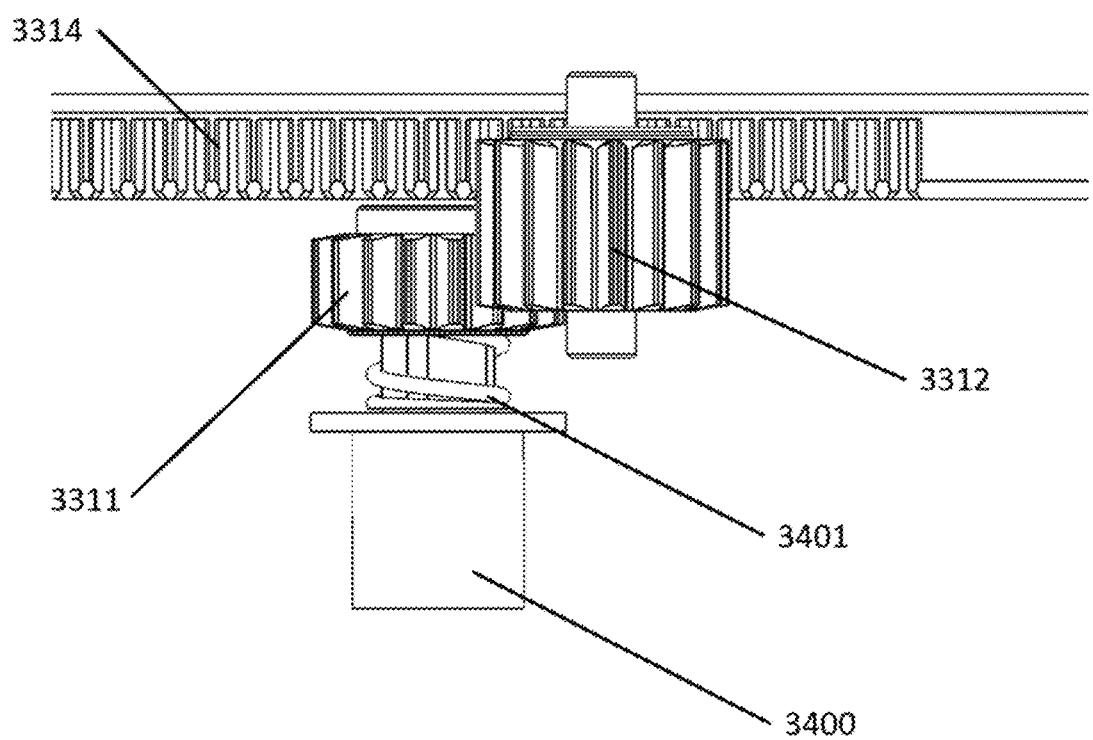
FIG. 26b is a schematic structural view of a transmission assembly according to an exemplary embodiment.

It should be appreciated that the first threaded rod 3354 of the above-mentioned embodiments may be replaced by a first sliding rod, and the above-mentioned resetting manner can also be implemented by sliding the first sliding rod which is fixedly connected to the second fixing member 3353 to move the second fixing member 3353. The second resetting tool 3350 can be implemented in various manners, which is not limited herein. The rotating motion output from the output end of the power assembly drives the first gear 3311 to rotate through the coupling 3400, and further converts into linear motion of the rack 3314 through the meshing between the first gear 3311 and the second gear 3312, and between the second gear 3312 and the rack 3314. Reference is also made to FIGS. 26a and 26b for a better view of the internal structural arrangement of the surgical instrument 1 and the interrelationship of the component parts.

Figure 27:
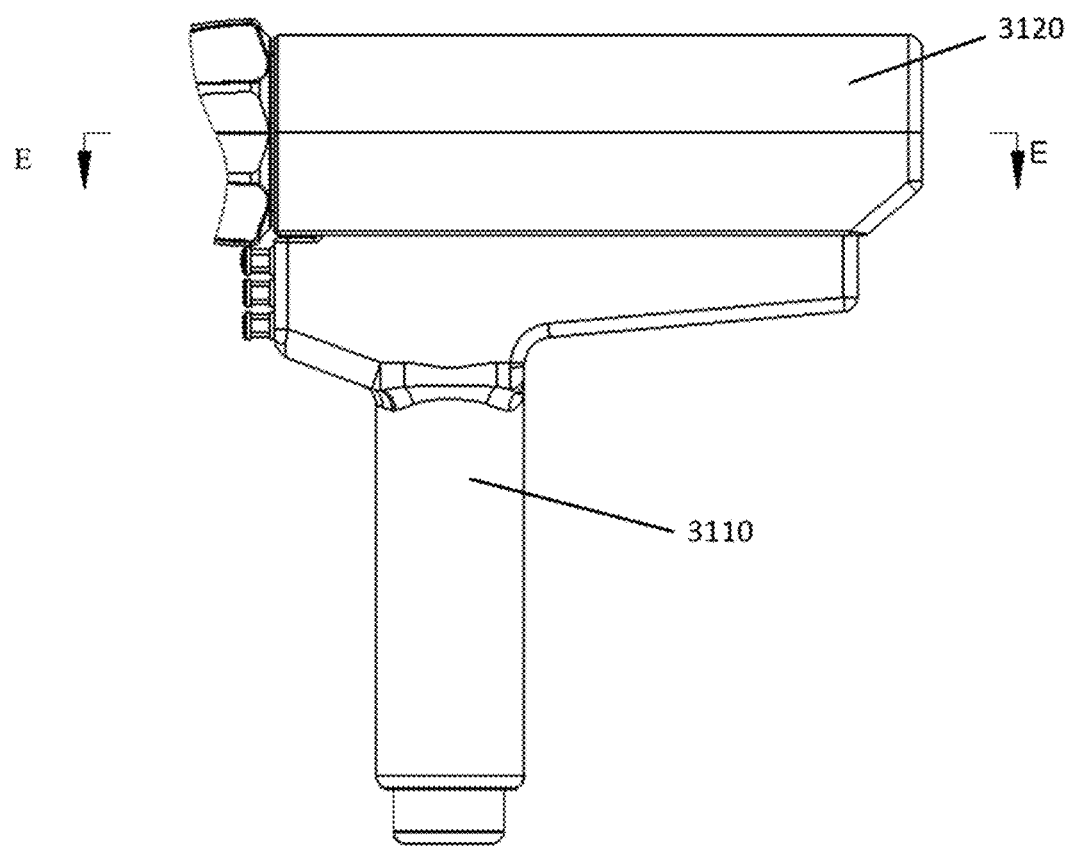
FIG. 27 is a schematic structural view of a control end according to an exemplary embodiment.
Figure 28:
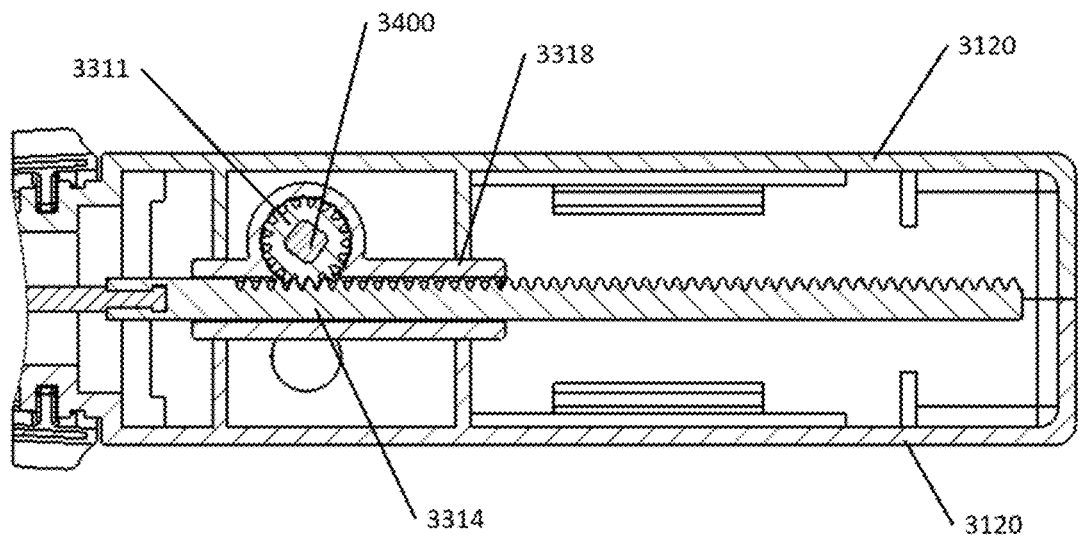
FIG. 28 is a schematic structural view of cross-section E according to an exemplary embodiment.
Figure 29:
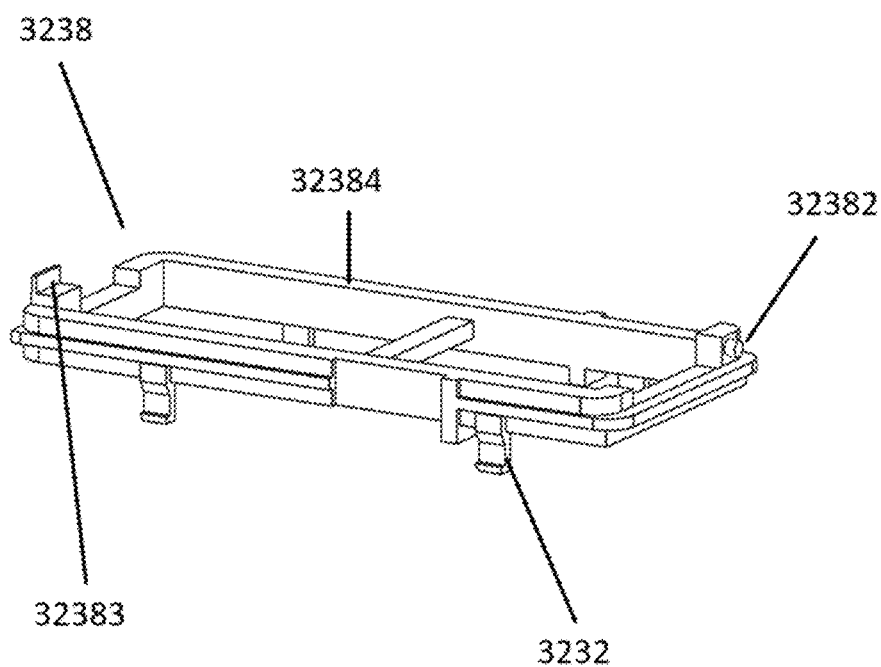
FIG. 29 is a schematic structural view of a connection body according to an exemplary embodiment.

In some embodiments, to further simplify the arrangement of the transmission assembly, as shown in FIG. 27, the power assembly 3200 is provided with an offset output end 3210, the output end 3210 being disposed coaxially with the coupling 3400.

The transmission assembly includes a first gear 3311 coaxially disposed with the coupling 3400, and the first gear 3311 is meshed with the rack 3314. The rotating output shaft drives the first gear 3311 to rotate through the coupling 3400, and further, the rotation is converted into linear motion of the rack 3314 through the meshing of the first gear 3311 and the rack 3314.

Figure 17:
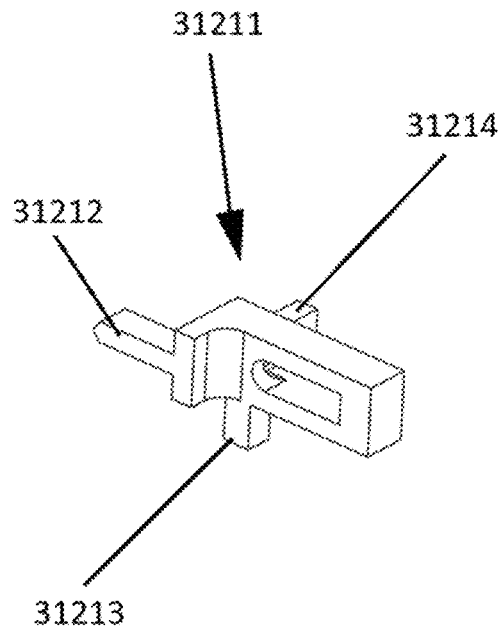
FIG. 17 is a schematic structural view of a rotating lock apparatus according to an exemplary embodiment.
Figure 18A:
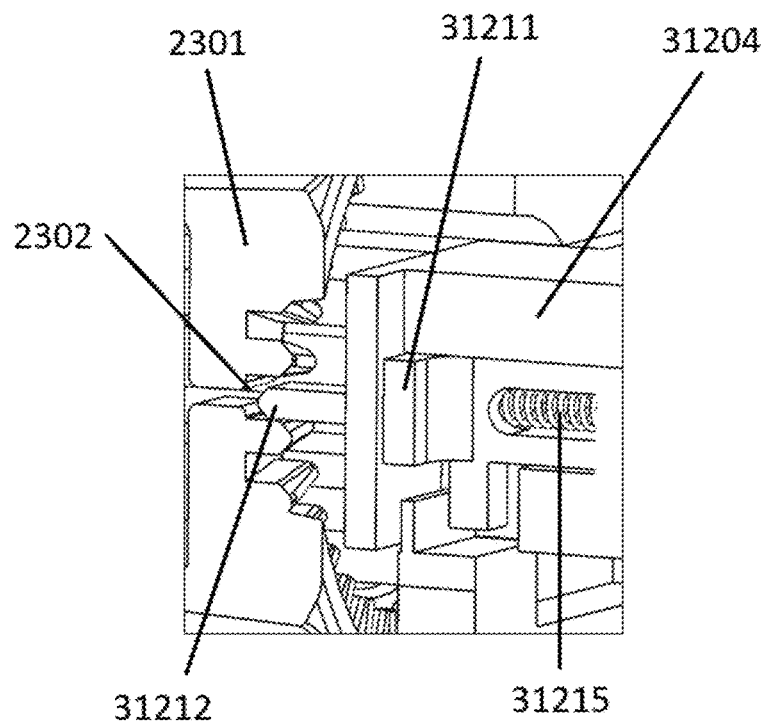
FIG. 18a is a schematic structural view of a rotating lock apparatus being inserted into a first groove of a rotating housing according to an exemplary embodiment.

In some embodiments, a gear frame 3318 is disposed within the second body 3120 to further limit the freedom of the first gear 3311 and the rack 3314. In some embodiments, to ensure that the user cannot operate the rotation mechanism 2300 when the end effector is operating to complete the desired action, the second body 3120 includes a rotating lock apparatus 31211 disposed within the first support 31204; and in some embodiments, as shown in FIG. 17, the rotating lock apparatus 31211 is provided with a disassembling lock portion 31213 and a firing lock portion 31214. As shown in FIG. 18a, the rotating lock apparatus 31211 is provided with one or more rotating lock portion 31212 thereon. It should be appreciated that the rotating housing 2301 of the rotating mechanism 2300 and the second body 3120 can rotate relative to each other, and that the rotating housing 2301 is provided with a toothed disc having at least one first groove 2302.

Figure 19A:
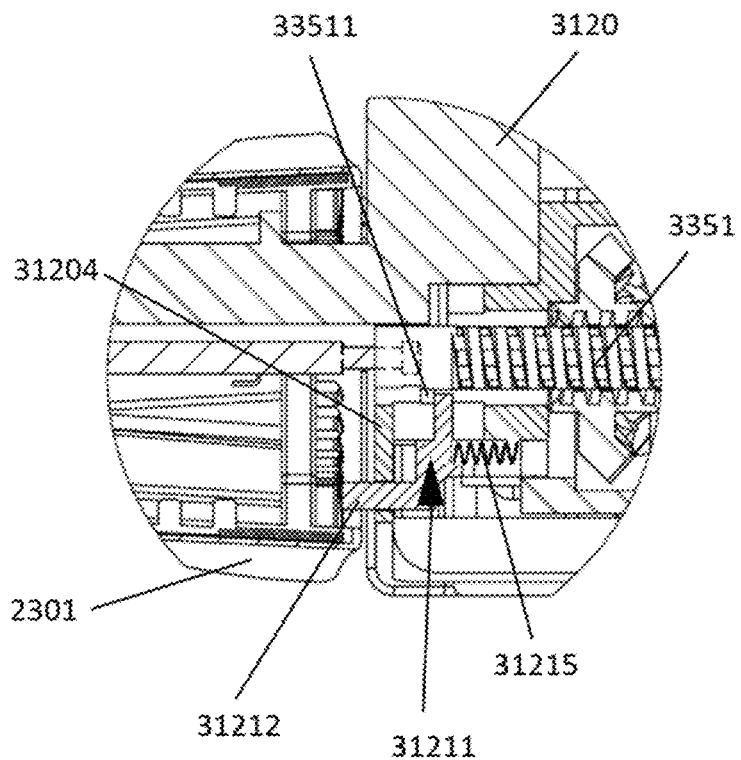
FIG. 19a is a cross-sectional view of a second body with a rotating lock apparatus being inserted into a first groove of a rotating housing according to an exemplary embodiment.
Figure 19B:
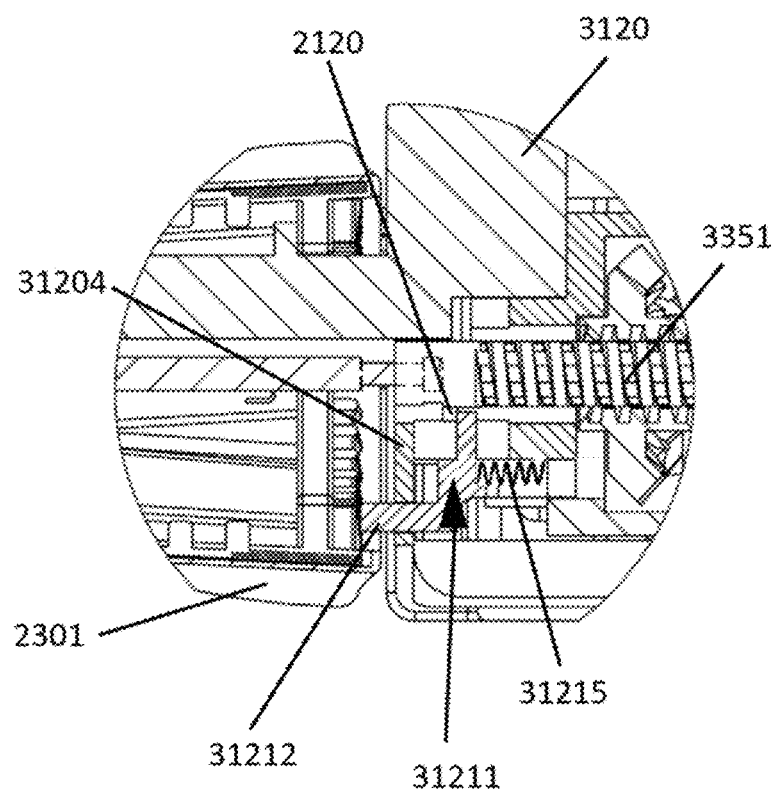
FIG. 19b is a cross-sectional view of a second body with a rotating lock apparatus being separated from a first groove of a rotating housing according to an exemplary embodiment.

In some embodiments, rotating lock apparatus 31211 operates in a manner specifically illustrated in FIG. 18a. A rotating lock spring 31215 is mounted within the rotating lock apparatus 31211, and one end of the rotating lock spring 31215 abuts against the second body 3120, and the other end abuts against the rotating lock apparatus 31211; the rotating lock apparatus 31211 is moved under the action of the rotating lock spring 31215. The rotating lock apparatus 31211 has two states in the movement, FIG. 19a shows an initial state of the rotating lock apparatus 31211, wherein the rotating lock apparatus 31211 is in a proximal position, the rotating lock spring 31215 is compressed, the rotating lock portion 31212 of the rotating lock apparatus 31211 is separated from the toothed disc of the rotating housing 2301, and the user can rotate the rotating housing 2301 to adjust the rotation angle of the end effector 2000. FIG. 19b illustrates an operation state of the rotating lock apparatus 31211, wherein the rotating lock apparatus 31211 is in the distal position, the rotating lock spring 31215 is in a relaxed or pre-stressed state, and the rotating lock portion 31212 of the rotating lock apparatus 31211 is inserted into the first groove 2302 of the rotating housing 2301, thus the rotating housing 2301 cannot be rotated.

Figure 18B:
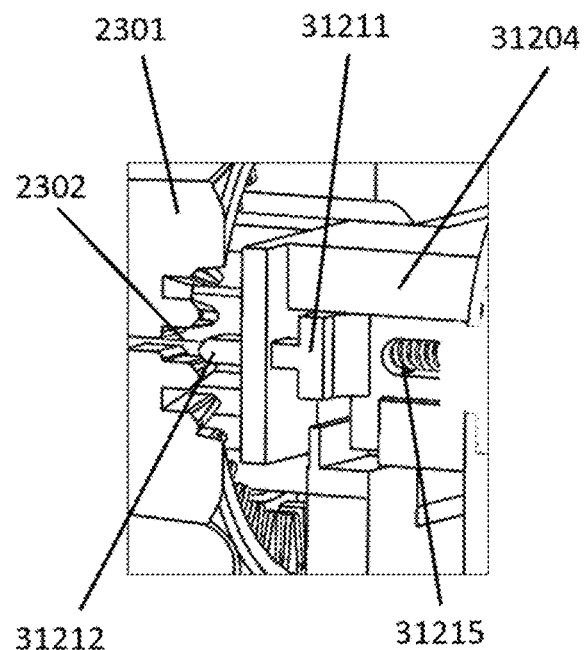
FIG. 18b is a schematic structural view of a rotating lock apparatus being separated from a first groove of a rotating housing according to an exemplary embodiment.

As shown in FIG. 18b, when the connection body 3238 moves towards the proximal end, the first lock portion 32383 of connection body 3238 abuts against the disassembling lock portion 31213 of rotating lock apparatus 31211 and pushes rotating lock apparatus 31211 to move towards the proximal end.

In some embodiments, the screw 3351 is provided with a ganged portion 33511, and when the screw 3351 moves towards the proximal end, the ganged portion 33511 of the screw 3351 abuts against the firing lock portion 31214 of the rotating lock apparatus 31211 to drive the rotating lock apparatus 31211 to move in the same direction, as shown in FIG. 19b. It will be appreciated that rack 3314 cooperates with rotation lock 31214 in a similar manner.

Figure 4A:
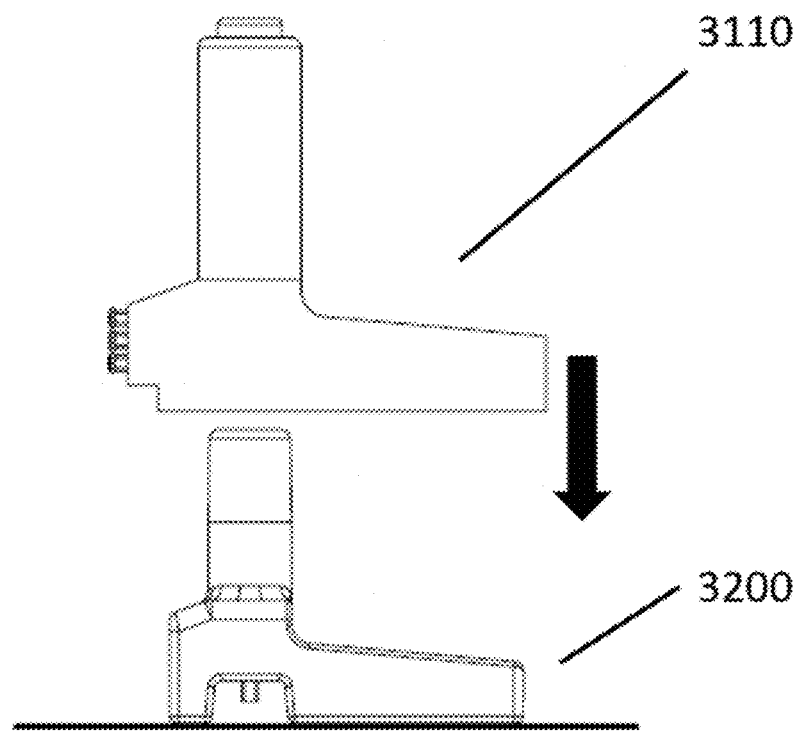
FIG. 4a is an assembly diagram of a first body and a power assembly according to an exemplary embodiment.
Figure 4B:
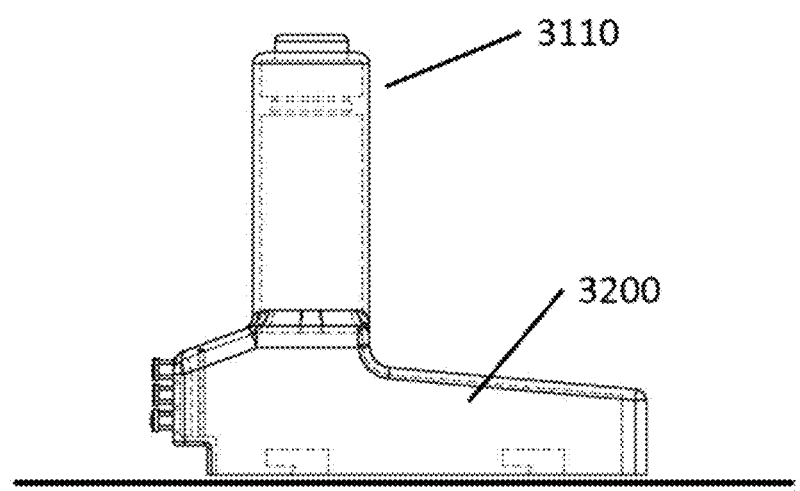
FIG. 4b is a completed assembly schematic diagram of a first body and a power assembly according to an exemplary embodiment.
Figure 5:
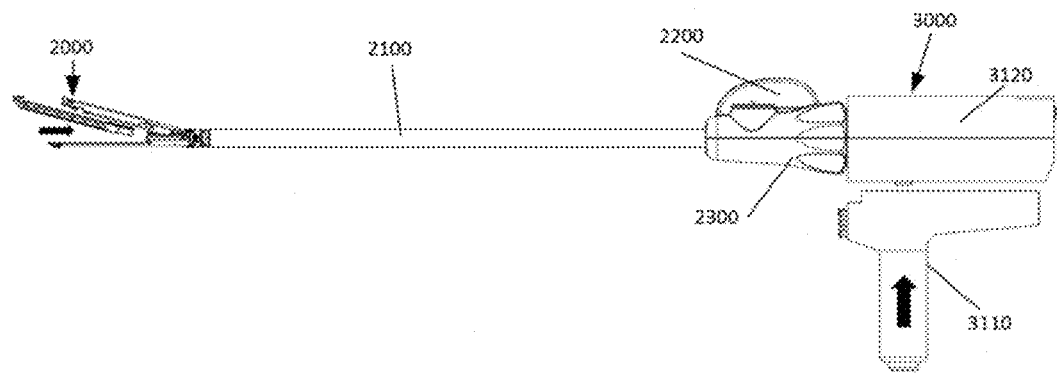
FIG. 5 is a schematic structural view of a surgical instrument according to an exemplary embodiment.

In some embodiments, when the power assembly 3200 is needed to be assembled with the first body 3110, as shown in FIG. 4a, the power assembly 3200 is first placed upside down on a workbench. The first body 3110 is placed upside down, aligned with power assembly 3200 from the top to the bottom, and assembled with power assembly 3200. During the operation and movement of the first body 3110, the power assembly 3200 is prevented from being separated from the first body 3110. Preferably, the dimension of the inner cavity at a certain position of the first body 3110 and the external dimension at a certain position of the power assembly 3200 are designed to be in interference fit, the sizes at the two positions are mutually matched when the first body 3110 and the power assembly 3200 are completely installed; since the friction force generated by the interference fit is greater than the gravity of the power assembly 3200, the two assemblies (as shown in FIG. 4b) cannot be separated. Next, as shown in FIG. 5, the first body 3110 combined with the power assembly 3200 is inserted into the second body 3120 from the bottom to the top, and the first body 3110 including the power assembly 3200 is connected to the second body 3120.

After the surgical instrument 1 is assembled, the desired operation of the surgical instrument 1 can be achieved by operating an operation switch.

The operation switch is an interactive interface between the user and equipment, and is mainly divided into two categories: keys which are used in the preparation stage and are not commonly used, e.g. a first control keys such as a switch and a setting key; and keys which are used for operating the surgical instrument 1 to perform different functions and are commonly used, e.g. a second control keys 3520 for firing, returning, securing, etc.

The first control key can be operated in the preparation stage of the operation and generally is no need for aseptic requirement; the generally first control key may be a touch key, such as a mechanical switch key, a dome array, a membrane switch, a pressure sensitive key, and a microkey, etc.

The second control key 3520 is typically operated during the surgical procedure to operate the surgical instrument 1 for different functions, typically with sterility requirements.

The operating portion of such operation switch is designed separately from the sensing portion of the signal. In this embodiment, the operating portion of the second control key 3520 is disposed in a disposable first body 3110, and the sensing portion is disposed in the reusable power assembly 3200 portion. Wherein, in some embodiments, the operating portion includes a button 3521, a keypress spring 3524, and a signal generator 3522; and the sensing portion includes a circuit board, and a signal sensing element 3523.

Figure 21:
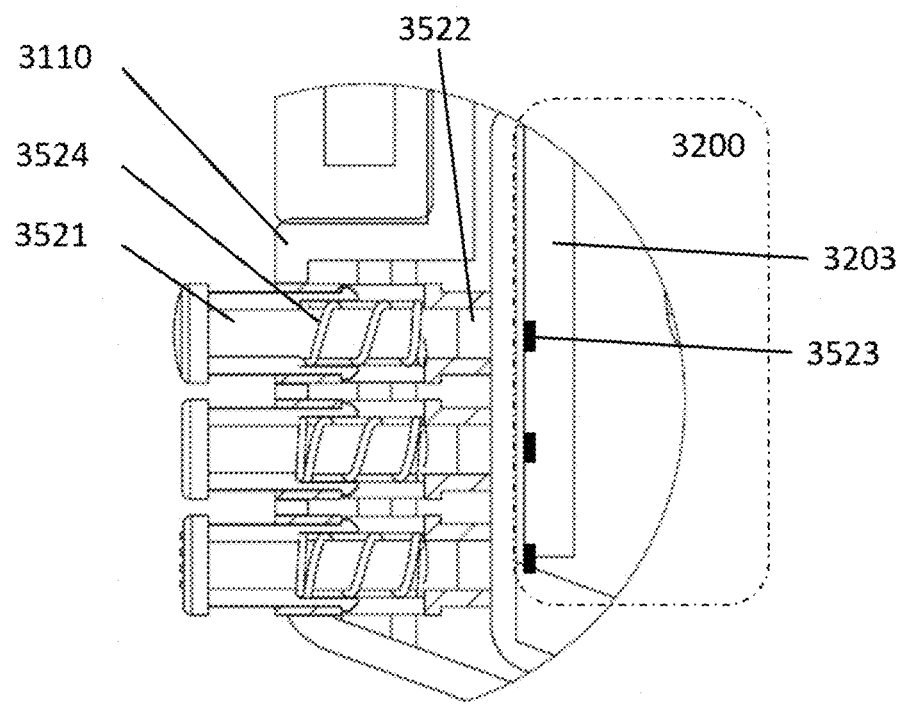
FIG. 21 is a schematic structural view of a second control key of a first body according to an exemplary embodiment.

As shown in FIG. 21, the signal generator of the operation switch of the first body 3110 is substantially aligned with the signal sensing element 3523 of the power assembly 3200. When the user presses the operation switch, the signal generator 3522 of the operation switch approaches the signal sensing element 3523, and the signal sensing element 3523 receives the sensing signal, the power assembly 3200 performs related information processing. When the user releases the operation switch, the signal generator 3522 of the operation switch is far away from the signal sensing element 3523, the signal is disconnected, and the power assembly 3200 performs related information processing.

The automatic resetting of the control switch is realized through a control switch spring.

The signal generator 3522 and signal sensing element 3523 may be one of the following combinations: magnetic materials and Hall devices, ferrous materials and inductance coils, electric conductors and capacitance devices, physical entities and ultrasonic sensing elements, physical entities and pressure sensing elements, which is not limited herein.

In accordance with the present embodiment, the surgical instrument 1 is provided with more than one second control key 3520, and the configuration of each second control key 3520 can be any of the configurations described above. The outer surfaces of the different buttons may be provided with different appearances, such as size, height, shape, color, surface state, etc., and the user may identify the different buttons by appearance or/and touch.

Figure 22:
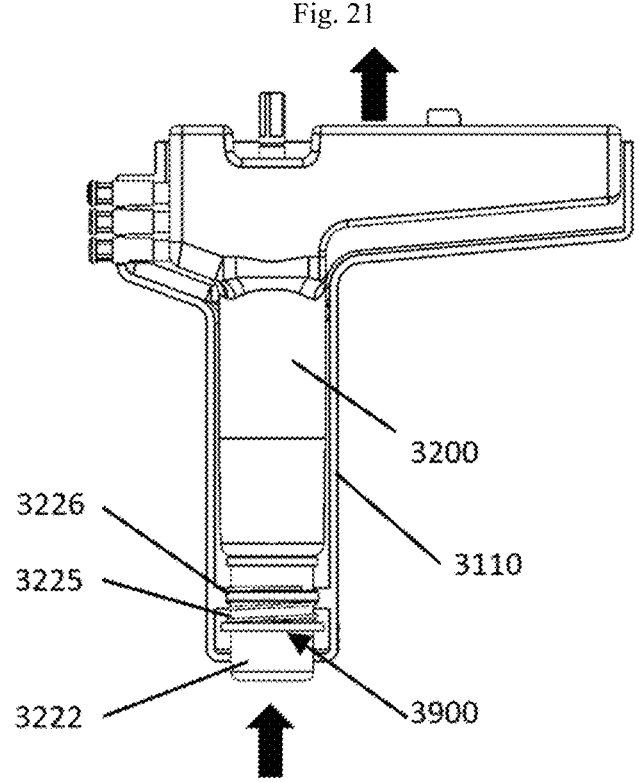
FIG. 22 is a schematic structural view of a first body of a movable member during use according to an exemplary embodiment.
Figure 23:
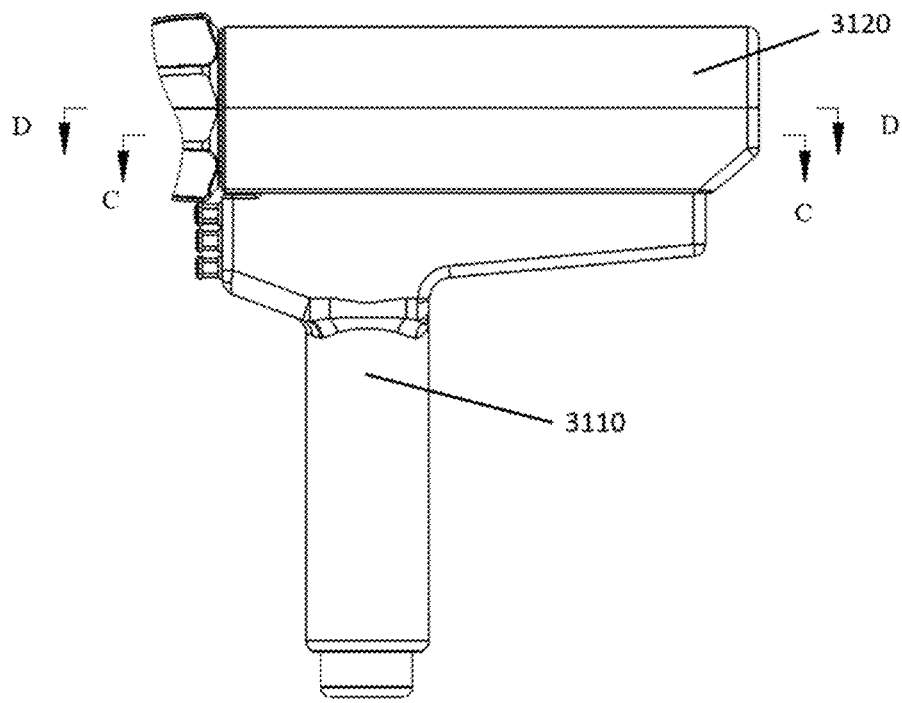
FIG. 23 is a schematic structural view of a control end according to an exemplary embodiment.

In some embodiments, as shown in FIG. 22, the surgical instrument 1 further includes a power assembly disassembling mechanism 3900. The power assembly disassembling mechanism 3900 includes a fourth guide channel disposed in the first body 3110 and a movable member 3222, the fourth guide channel is provided with a third opening, the movable member 3222 is located in the fourth guide channel, one end of the movable member 3222 passes through the third opening, the other end of the movable member 3222 abuts against the power assembly 3200, and the power assembly 3200 is separated from the first body 3110 by actuating the movable member 3222. In the meanwhile, the movable member 3222 may be considered as a key, and the power assembly 3200 may be pushed out of the first body 3110 by depressing the movable member 3222.

In some embodiments, the movable member 3222 abuts against the first body 3110 (more specifically, inside the housing of the first body 3110) through the third resetting spring 3225, one end of the third resetting spring 3225 abuts against the movable member 3222, and the other end of the third resetting spring 3225 abuts against the first body 3110, such that after pressing the movable member 3222, the movable member 3222 may be driven to return to the original position.

In some embodiments, a sealing ring 3226 is disposed on the movable member 3222 for the sealing effect of the first body 3110.

Figure 38A:
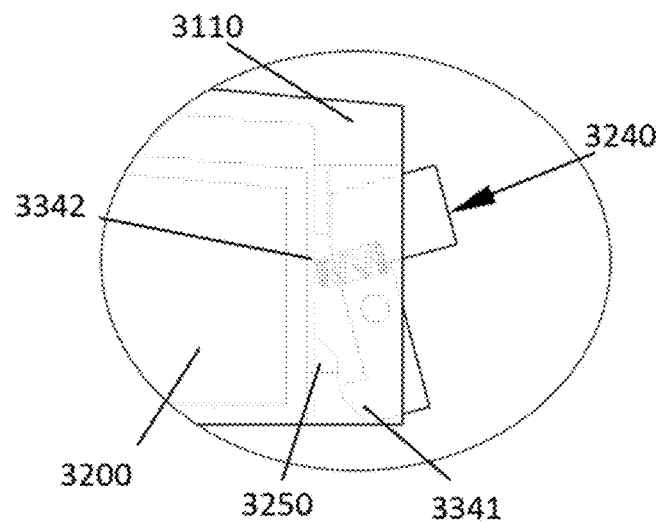
FIG. 38a is a schematic structural view of a push-button member and a first snap member (with a power assembly ready to be inserted into a first body) according to an exemplary embodiment.
Figure 38B:
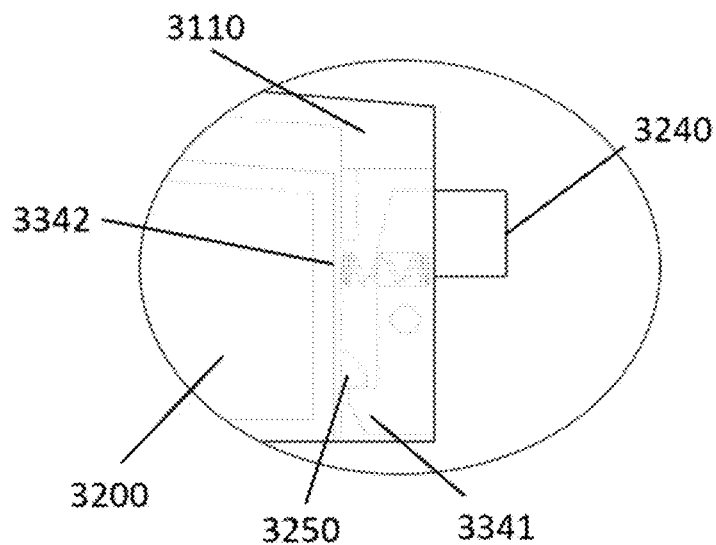
FIG. 38b is a schematic structural view of a push-button member and a first snap member (with a power assembly completely being inserted into a first body) according to an exemplary embodiment.
Figure 39A:
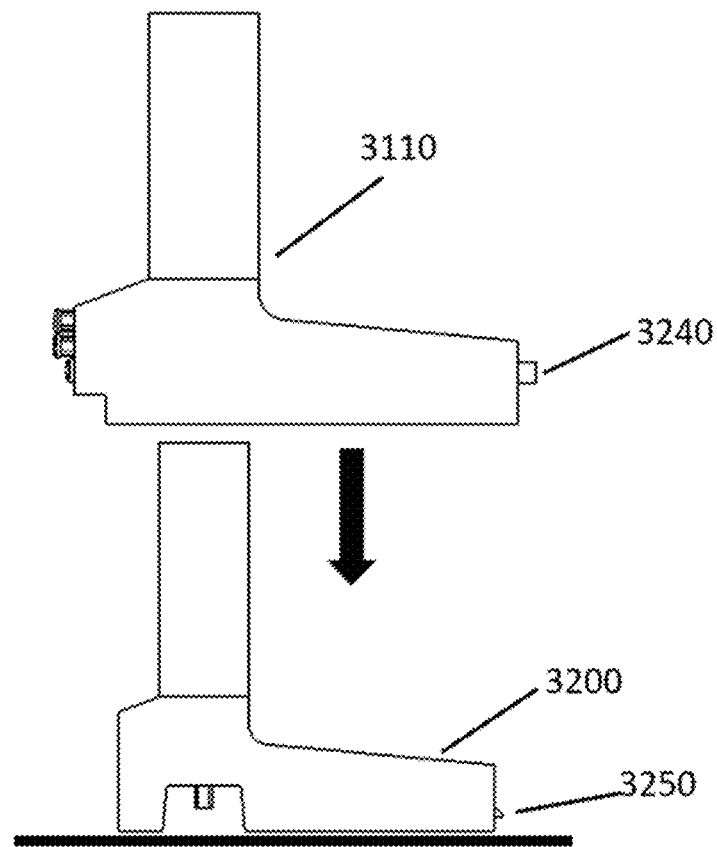
FIG. 39a is an assembly view of a power assembly ready to be inserted into a first body according to an exemplary embodiment.
Figure 39B:
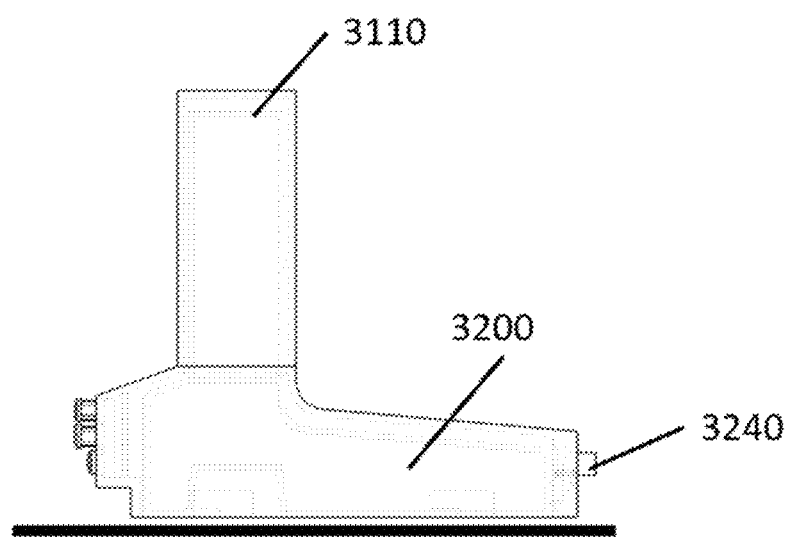
FIG. 39b is an assembly view of a power assembly into a first body according to an exemplary embodiment.
Figure 40:
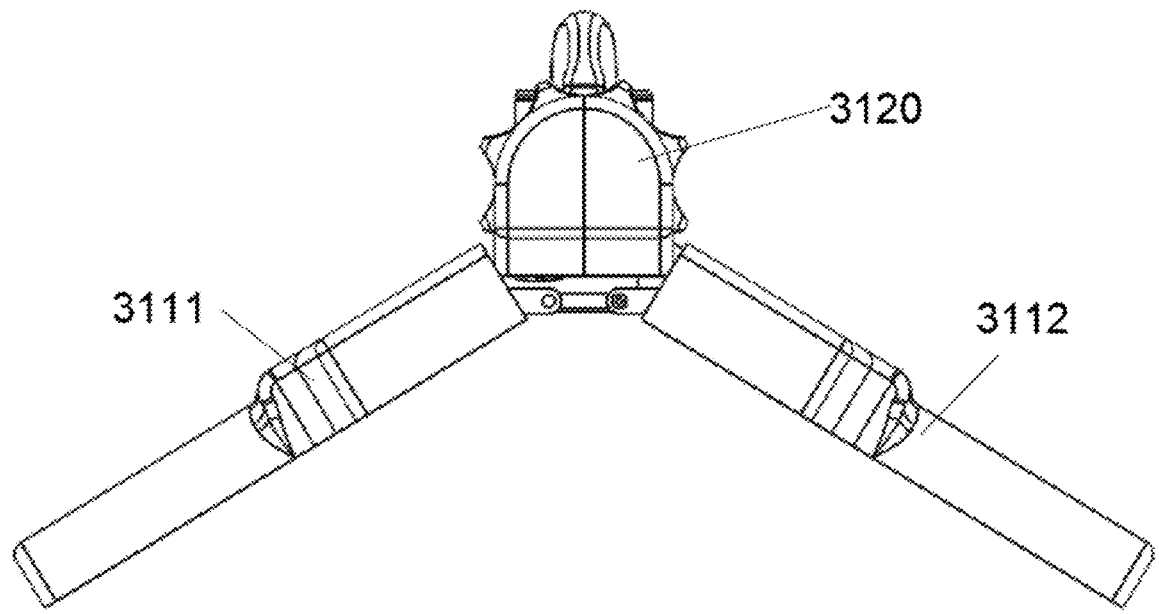
FIG. 40 is a schematic structural view of a housing of an end effector according to an exemplary embodiment.
Figure 41:
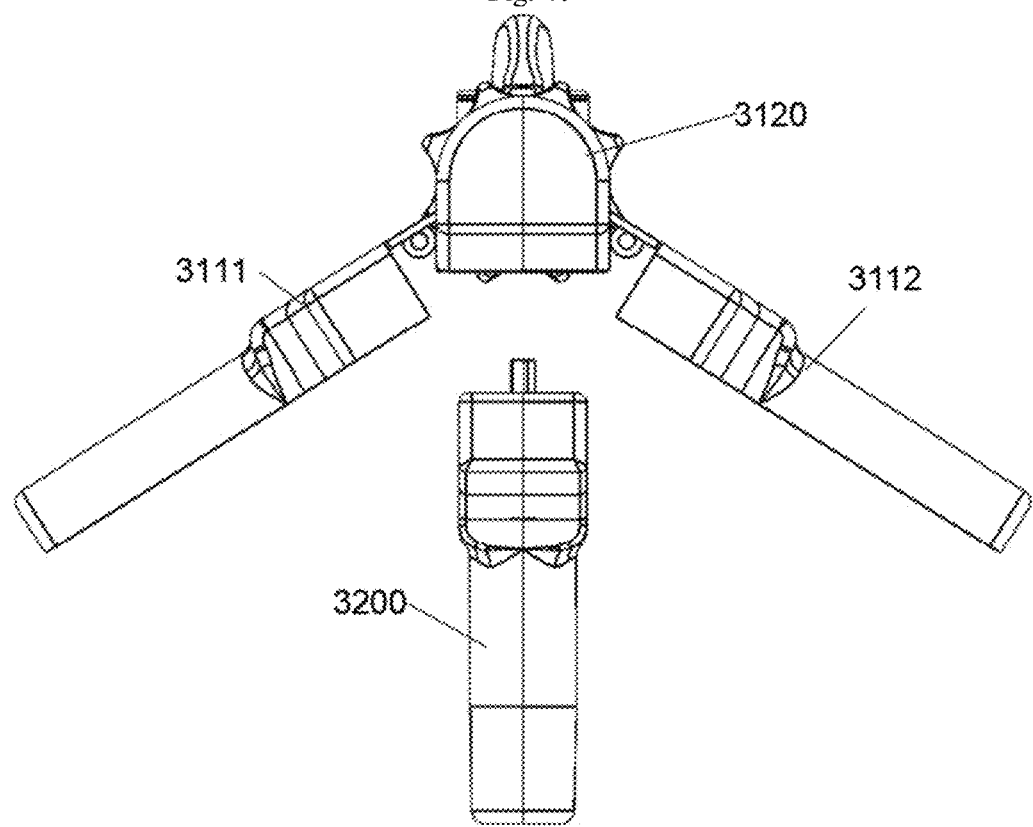
FIG. 41 is a schematic structural view of a first assembly and a second assembly in combination with a power assembly according to an exemplary embodiment.
Figure 42:
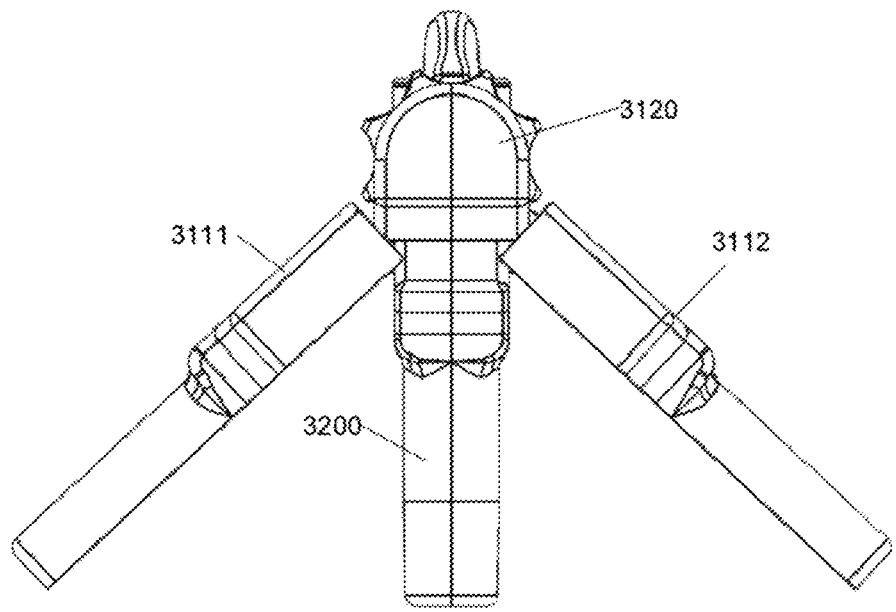
FIG. 42 is a schematic structural view of a first assembly and a second assembly in combination with a power assembly according to an exemplary embodiment.
Figure 43:
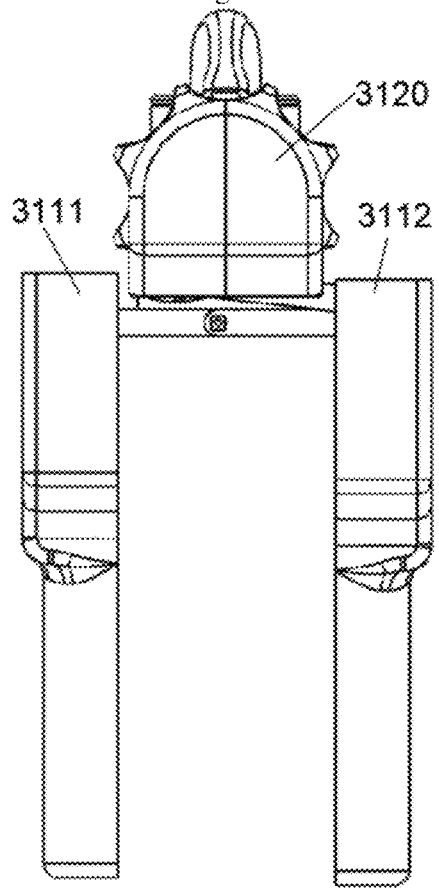
FIG. 43 is a schematic structural view of a housing of an end effector according to an exemplary embodiment.
Figure 44:
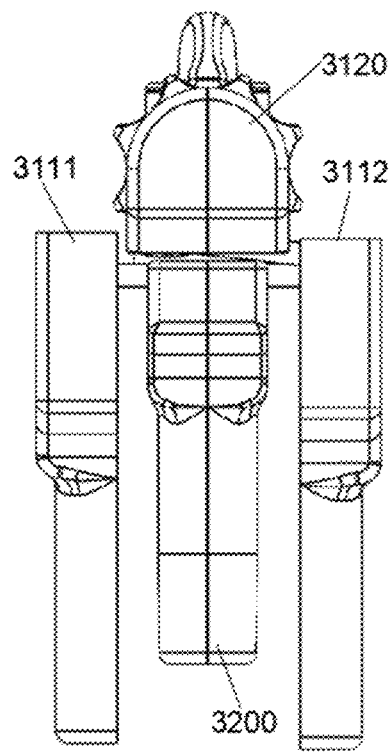
FIG. 44 is a schematic structural view of a first assembly and a second assembly in combination with a power assembly according to an exemplary embodiment.

As the power assembly 3200 and the first body 3110 can be assembled in various ways, in some embodiments, the power assembly 3200 and the first body 3110 can be assembled as shown in FIGS. 37-39. Firstly, the power assembly 3200 is placed upside down on the workbench. A sterile first body 3110 is placed upside down, aligned with power assembly 3200 from the top to the bottom, and assembled with power assembly 3200. During operational movement of the first body 3110, the power assembly 3200 is prevented from being separated from the first body 3110 by a snap-lock mechanism.

Figure 37A:
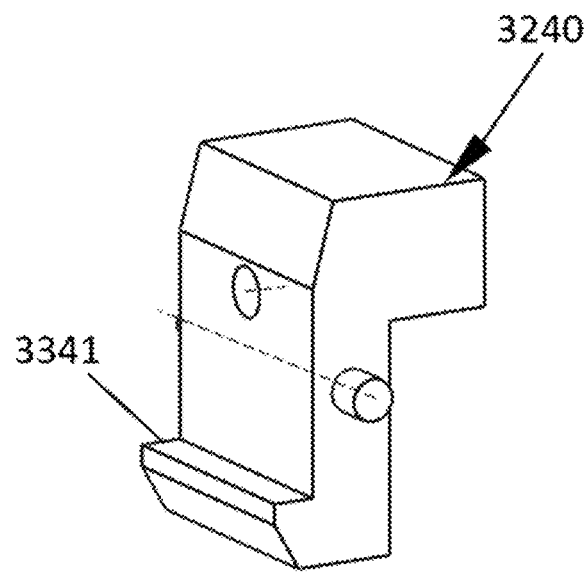
FIG. 37a is a schematic structural view of a push-button member according to an exemplary embodiment.
Figure 37B:
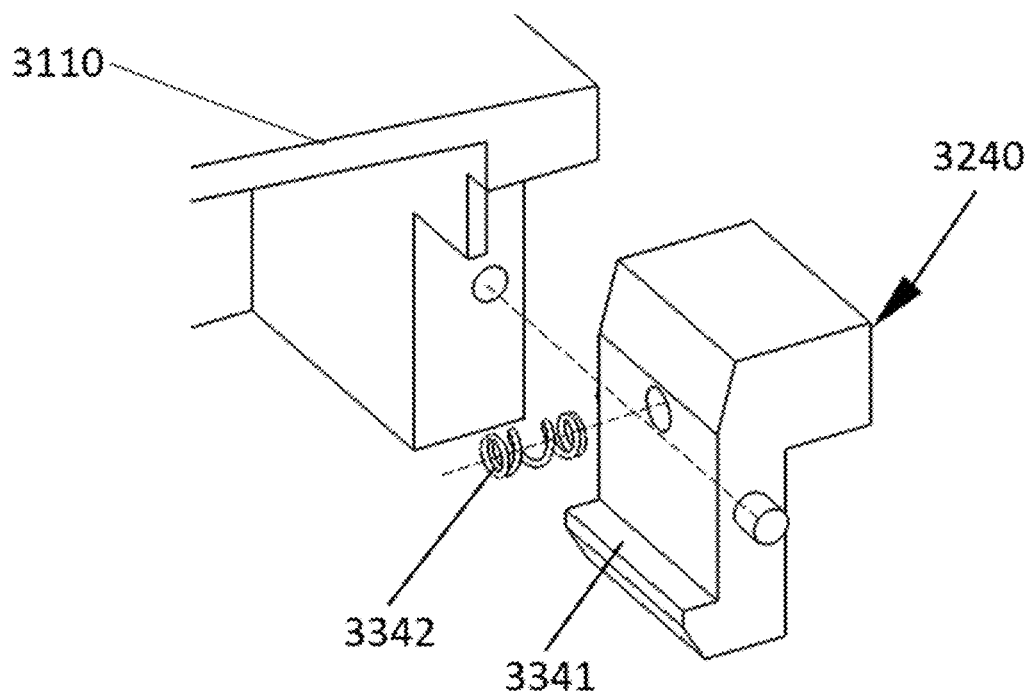
FIG. 37b is a schematic structural view of a push-button member and a first body according to an exemplary embodiment.

As shown in FIGS. 37a and 37b, the push-button member 3240 is provided with a third snap member 3241, a rotating shaft, and a tenth spring 3342. The tenth spring 3342 is mounted on a push-button member 3240, and the push-button member 3240 is rotatably mounted on the first body 3110 through the rotating shaft. The button may be pressed to release the engagement of the push-button member 3240 with the first body 3110 when the first body 3110 and the power assembly 3200 need to be separated, and the power assembly 3200 may be easily taken out as shown in FIG. 39a.

As shown in FIGS. 38a and 38b, the power assembly 3200 is provided with a first snap member 3250, and the first body 3110 is provided with a push-button member 3240. When the first body 3110 and the power assembly 3200 are installed, one end of the tenth spring 3342 abuts against the push-button member 3240, and the other end of the tenth spring 3342 abuts against the first body 3110, thus the push-button member 3240 rotates under the action of the third snap member 3241 and the first snap member 3250 to compress the tenth spring 3342, as shown in FIG. 38a. After the first body 3110 is pushed to the predetermined position, as shown in FIG. 38b, the push-button member 3240 is reset under the action of the tenth spring 3342, and the third snap member 3241 and the first snap member 3250 are connected to each other by snap engagement, as shown in FIG. 38b, in the meanwhile, the power assembly 3200 is not separated from the first body 3110.

It should be appreciated that the first body 3110 and the second body 3120 can be connected in various ways, and as shown in FIGS. 29-36, in some embodiments, the connection body 3238 is provided with a snap connection portion 3232, a disassembling protrusion portion 32381, a spring mounting portion 32382, a first lock portion 32383, and a guide protrusion 32384, wherein the number of the snap connection portions 3232 is not limited as long as the number is not less than 1, and the number of the disassembling protrusion portions 32381 is not limited as long as the number is not less than 1.

Figure 31A:
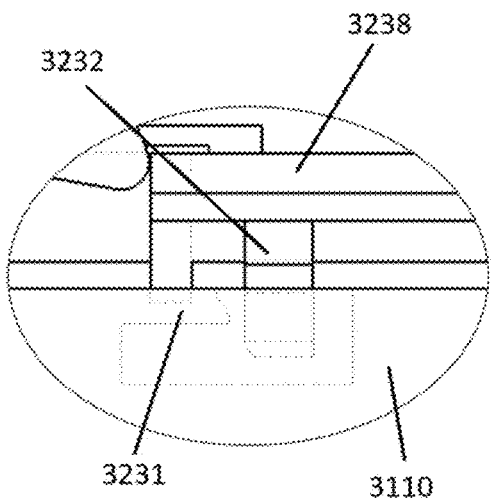
FIG. 31a is a schematic view of partial structure of a snap connection portion and a snap portion of a first actuating mechanism during use (with the snap connection portion and the snap portion ready to be disengaged from each other) according to an exemplary embodiment.

The connection body 3238 is disposed in the second body 3120, and a second resetting spring 32385 is installed to the proximal end of the connection body 3238. The first body 3110 is provided with a snap portion 3231 which is engaged with a snap connection portion 3232 of the connection body 3238 when the first body 3110 is assembled, as shown in FIG. 31a, in the meanwhile the second body 3120 is locked with the first body 3110, thereby completing the assembly of the surgical instrument 1.

Figure 30:
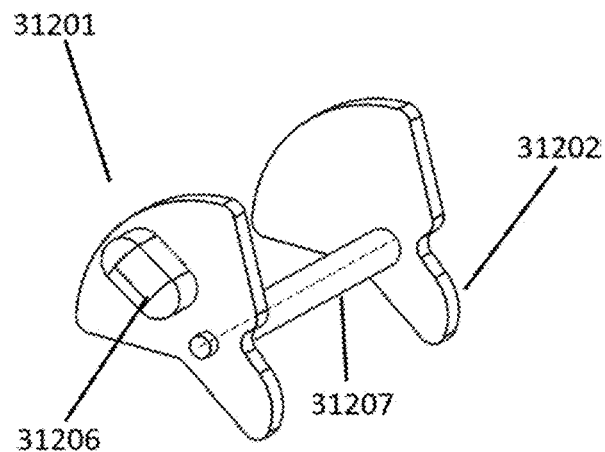
FIG. 30 is a schematic structural view of a first actuating mechanism according to an exemplary embodiment.

In some embodiments, as shown in FIG. 30, the first actuating mechanism 31201 is provided with two cams 31202, two disassembling toggles 31206 and one third rotating shaft 31207, and the number of the cams 31202 is not limited to 2, as long as the number of the cams is not less than 1. The cams 31202 are connected by the third rotating shaft 31207, and the disassembling toggles 31206 are provided on the cams 31202.

Figure 31B:
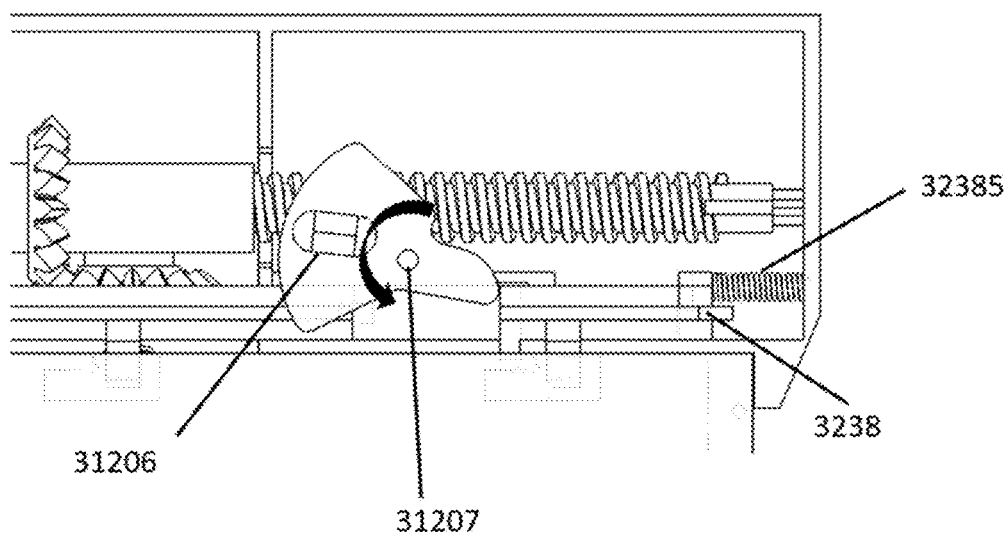
FIG. 31b is a schematic view of overall structure of a snap connection portion and a snap portion of a first actuating mechanism during use (with the snap connection portion and the snap portion ready to be disengaged from each other) according to an exemplary embodiment.
Figure 32A:
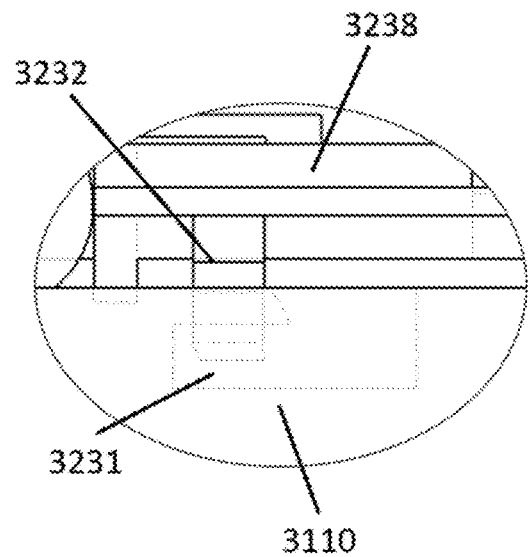
FIG. 32a is a schematic view of partial structure of a snap connection portion and a snap portion of a first actuating mechanism during use (with the snap connection portion and the snap portion being connected) according to an exemplary embodiment.
Figure 32B:
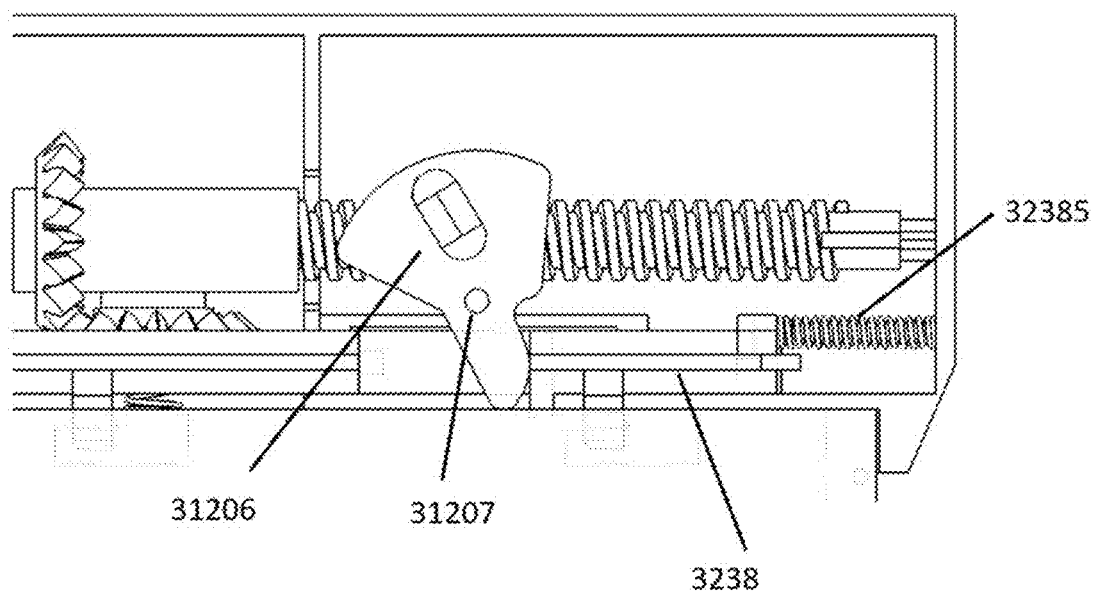
FIG. 32b is a schematic view of overall structure of a snap connection portion and a snap portion of a first actuating mechanism during use (with the snap connection portion and the snap portion being connected) according to an exemplary embodiment.

The first actuating mechanism 31201 is rotatably installed in the second body 3120, and when the first body 3110 and the second body 3120 are installed and locked, the first actuating mechanism 31201 is as shown in FIG. 32a. The disassembling toggle 31206 is pressed to the state shown in FIG. 32b, the cam 31202 connected to the disassembling toggle 31206 pushes the connection body 3238 to the right, such that the snap portion 3231 of the first body 3110 is disengaged from the snap connection portion 3232 of the connection body 3238 (as shown in FIG. 31b), and in the meanwhile, the first body 3110 and the second body 3120 can be separated, such that the first body 3110 and the second body 3120 are in the second state.

Figure 33:
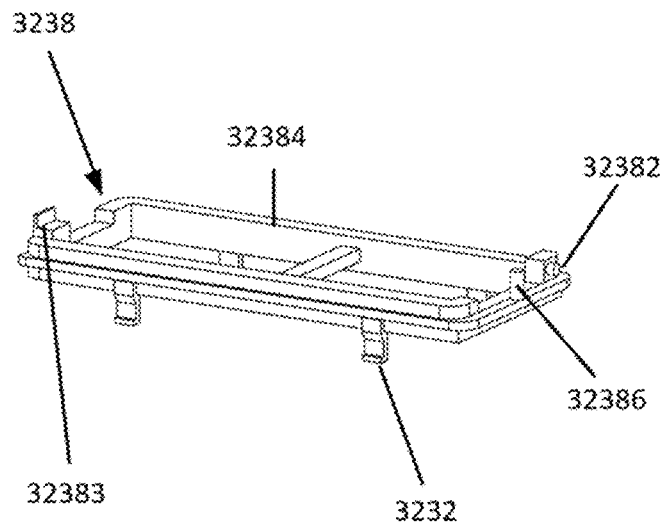
FIG. 33 is a schematic structural view of a connection body according to an exemplary embodiment.

In some embodiments, as shown in FIG. 33, the connection body 3238 is provided with the snap connection portion 3232, a first fixing pillar 32386, a spring mounting portion 32382, a first lock portion 32383 and a guide protrusion 32384, wherein the number of the snap connection portion 3232 is not limited to 4, as long as the number is not less than 1.

Figure 35A:
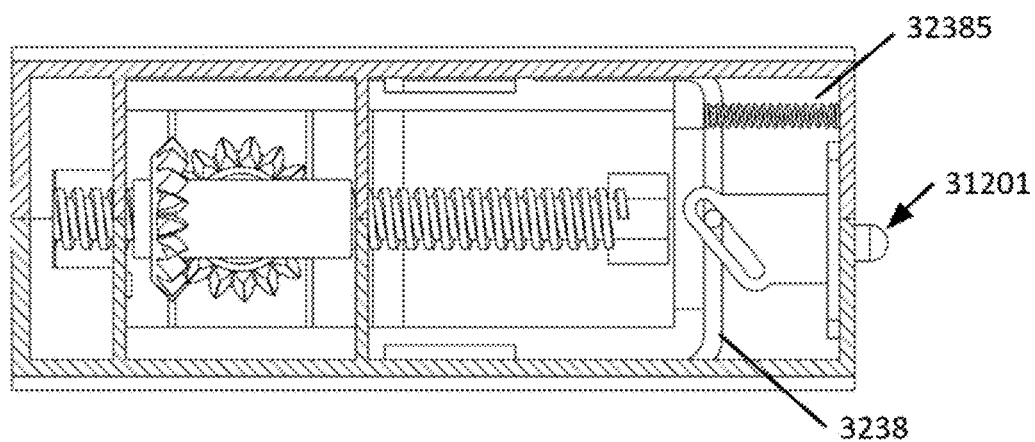
FIG. 35a is a schematic structural view of a connection body and a first actuating mechanism being mated (with a snap portion and a snap connection portion being connected) according to an exemplary embodiment.
Figure 35B:
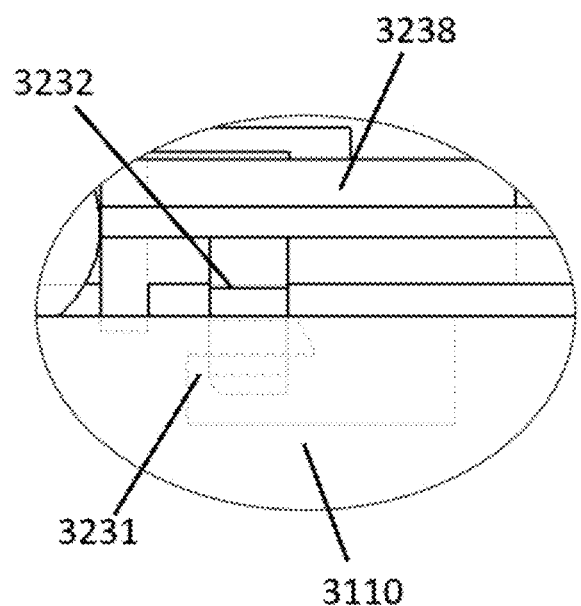

The connection body 3238 is disposed in the second body 3120, and the second resetting spring 32385 is mounted to the proximal end of the connection body 3238. The first body 3110 is provided with the snap portion 3231 which is engaged with the snap connection portion 3232 of the connection body 3238 when the first body 3110 is assembled, as shown in FIG. 35b, and the second body 3120 is locked with the first body 3110, thereby completing the assembly of the surgical instrument 1.

Figure 34:
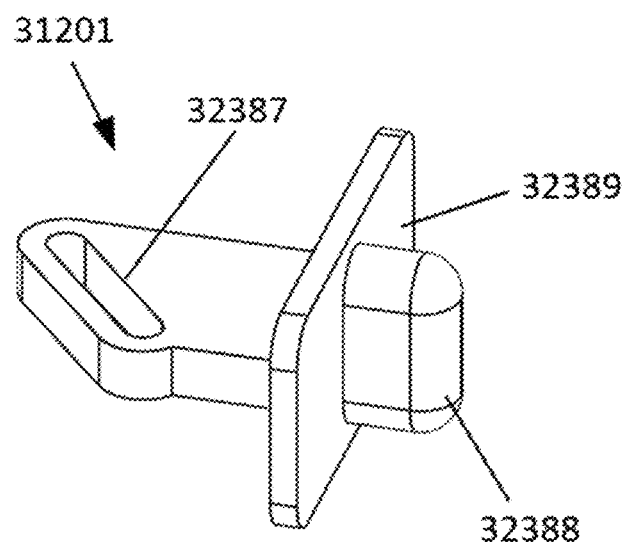
FIG. 34 is a schematic structural view of a first actuating mechanism according to an exemplary embodiment.

In some embodiments, as shown in FIG. 34, the first actuating mechanism 31201 is provided with a sliding chute 32387 and a toggle 32388. The first actuating mechanism 31201 is slidably disposed on the connection main body 3238 through the matching of the sliding chute 32387 and the first fixing pillar 32386. The first actuating mechanism 31201 is further provided with a baffle plate 32389 for guiding the first actuating mechanism 31201 to move along a preset direction.

Figure 36A:
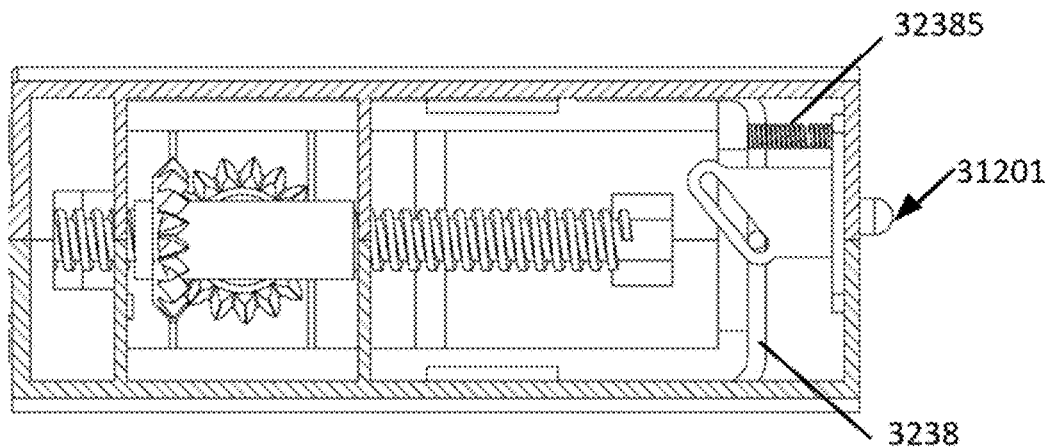
FIG. 36a is a schematic view of a connection body and a first actuating mechanism engaged according to an exemplary embodiment (with a snap portion disengaged from a snap connection portion).
Figure 36B:
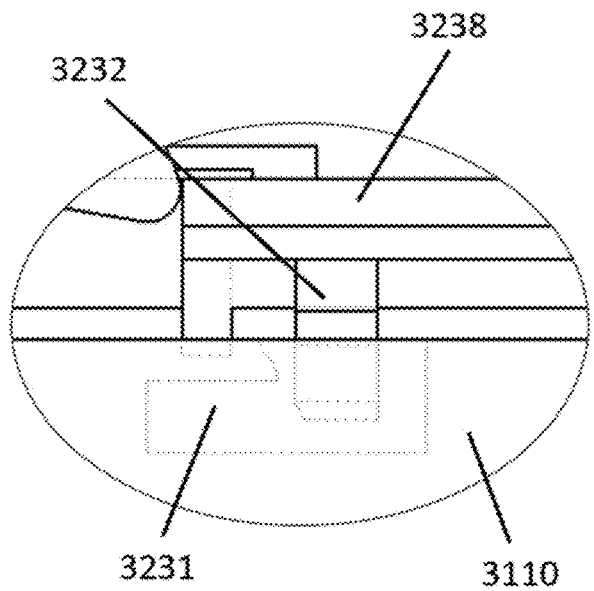

The first actuating mechanism 31201 is slidably installed in the second body 3120, and when the first body 3110 and the second body 3120 are installed and locked, the first actuating mechanism 31201 is as shown in FIG. 36a. When the disassembling toggle 31206 is moved to the state shown in FIG. 36b, the sliding chute 32387 of the disassembling toggle 31206 pushes the connection body 3238 to the right, such that the snap portion 3231 of the first body 3110 is disengaged with the snap connection portion 3232 of the connection body 3238 (as shown in FIG. 36b), and in the meanwhile, the first body 3110 is separated from the second body 3120.

In some embodiments, the control end 3000 further includes a turning control mechanism 2200, and the turning control mechanism 2200 includes a turning control spanner 2210 and a turning control rotating body 2220. The end effector assembly 2400 is controlled to turn to a certain degree by the turning control spanner 2210 and the turning control rotating body 2220.

In some embodiments, as shown in FIGS. 40-44, a first body 3110 includes a first assembly 3111 and a second assembly 3112, wherein the first assembly 3111 and the second assembly 3112 can be open according to a certain track, then the power assembly 3200 is inserted into a second body 3120, and then the first assembly 3111 and the second assembly 3112 are closed according to a certain track; finally, the power assembly 3200 is assembled by the cooperation of the first assembly 3111, the second assembly 3112 and the second body 3120. In the meanwhile, the first body 3110 and the second body 3120 are in the first state.

Figure 45A:
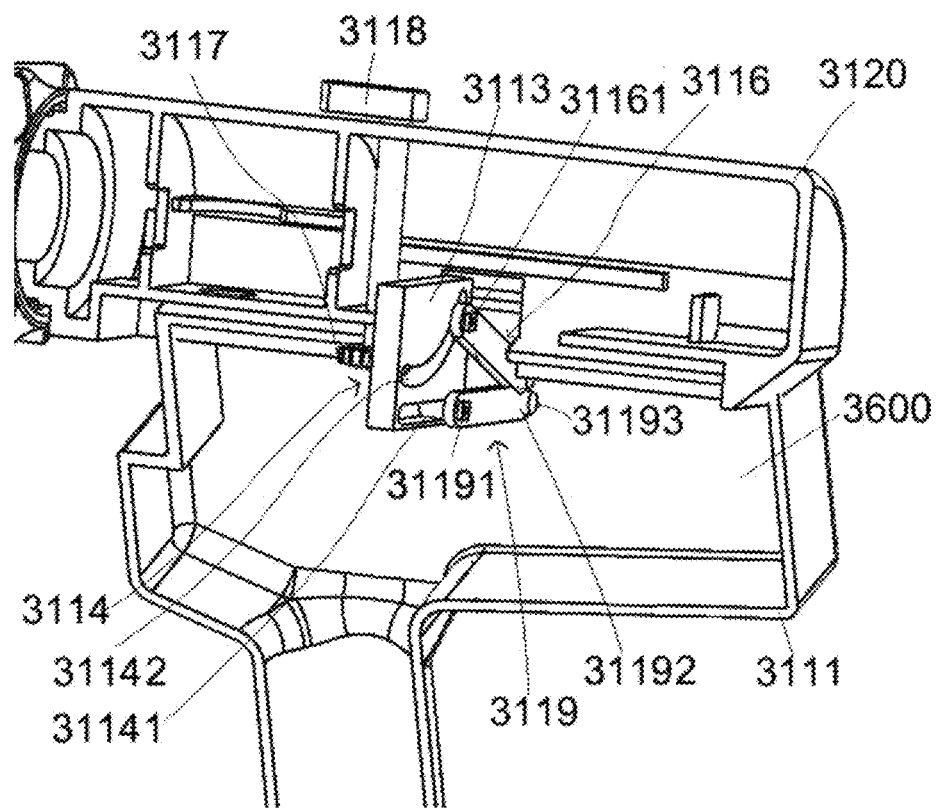
FIG. 45a is a schematic structural view of an internal structure of a housing of an end effector according to an exemplary embodiment.
Figure 45B:
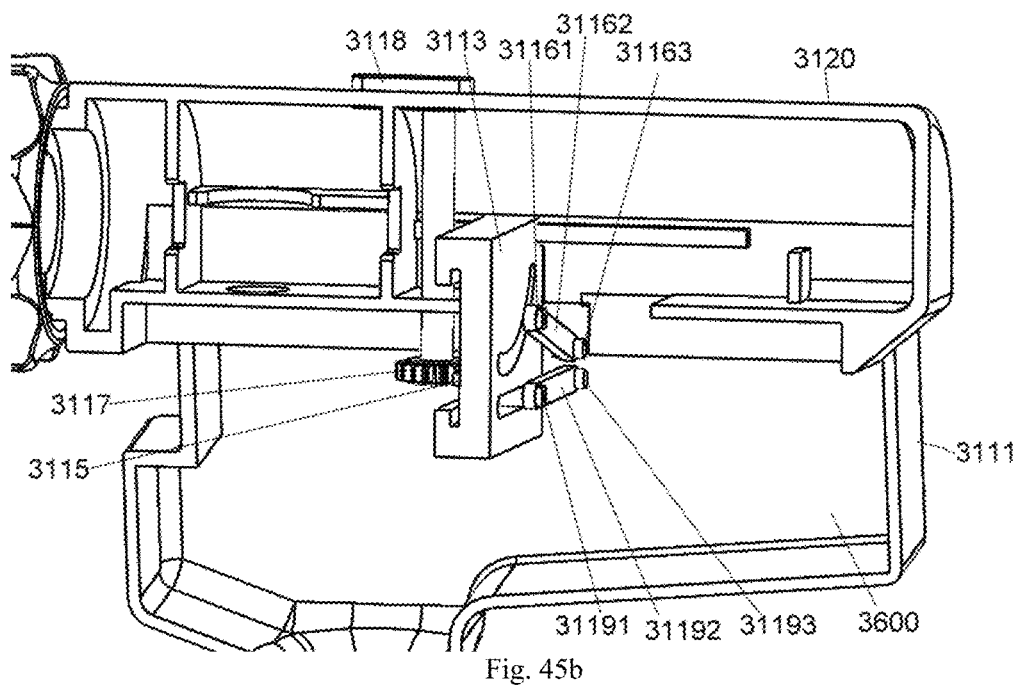
FIG. 45b is a schematic structural view of an internal structure of a housing of an end effector according to an exemplary embodiment.

Meanwhile, as shown in FIGS. 45a and 45b, the second body 3120 further includes a guide structure 3113, and the guide structure 3113 includes a first guide body 3114, wherein the guide body 3114 is provided with a first guide groove 31141 and a second guide groove 31142; the first assembly 3111 and second assembly 3112 are provided with a first buckling portion 3119 and slidably coupled to the first guide groove 31141 through the first buckling portion 3119, and the first assembly 3111 and second assembly 3112 are provided with a second buckling portion 3116 and slidably coupled to the second guide groove 31142 through the second buckling portion 3116, thereby the first assembly 3111 and second assembly 3112 realize the open and close between the first assembly 3111 and second assembly 3112 by being engaged with the guide structure 3113, and when the first assembly 3111 and second assembly 3112 are closed, the first body 3110 and the second body 3120 are in the first state, and the first assembly 3111, the second assembly 3112 and the second body 3120 cooperate with each other to form a closed or even sealed first cavity 3600. In some embodiments, when the first assembly 3111 is separated from the second assembly 3112 and in the second state, the first cavity 3600 is open.

Figure 45C:
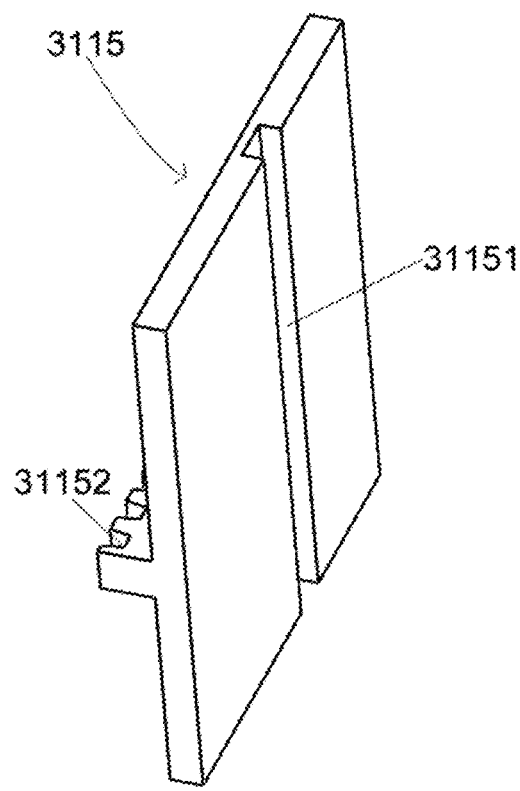
FIG. 45c is a schematic structural view of a second guide body according to an exemplary embodiment.

In some embodiments, taking the first assembly 3111 as an example, as shown in FIG. 45a, FIG. 45b and FIG. 45c, the first buckling portion 3119 of the first assembly 3111 includes a first moving end 31191 and a first connection bar 31192; wherein, one end of the first moving end 31191 is fixedly connected to one end of the first connection bar 31192, and the other end of the first moving end 31191 passes through the first guide groove 31141, such that the first moving end 31191 is slidably disposed in the first guide groove 31141, and the other end of the first connection bar 31192 is hinged to the first assembly 3111 through the third rotating shaft 31193; the second buckling portion 3116 of the first assembly 3111 includes a second moving end portion 31161 and a second connection bar 31162, wherein one end of the second moving end portion 31161 is hinged to one end of the second connection bar 31162, the other end of the second moving end portion 31161 passes through the second guide groove 31142, such that the second moving end portion 31161 is slidably disposed in the second guide groove 31142, the other end of the second connection bar 31162 is hinged to the first assembly 3111 through a fourth rotating shaft 31163, the third rotating shaft 31193 is fixedly connected to the first assembly 3111, the fourth rotating shaft 31163 is fixedly connected to the first assembly 3111, and the extending path of the first guide groove 31141 is different from that of the second guide groove 31142. When the first moving end 31191 and the second moving end 31161 are pushed simultaneously according to the preset moving manner, since the extending paths of the first guide groove 31141 and the second guide groove 31142 are different, the angle between the second connection bar 31162 and the first connection bar 31192 is changed, such that the direction of the pulling force of the second connection bar 31162 to the fourth rotating shaft 31163 and the direction of the pulling force of the first connection bar 31192 to the third rotating shaft 31193 are different, so the first assembly 3111 is driven to rotate. In some embodiments, the third rotating shaft 31193 and the fourth rotating shaft 31163 are parallel to each other, and the moving directions of the first moving end 31191 and the second moving end 31161 are perpendicular to the extending directions of the third rotating shaft 31193 and the fourth rotating shaft 31163.

In some embodiments, as shown in FIG. 45b, the guide structure 3113 further includes a second guide body 3115, and the first moving end 31191 and the second moving end 31161 are moved by the second guide body 3115. More specifically, the second guide body 3115 is provided with a third guide groove 31151, and the other end of the first moving end 31191 is passing through the first guide groove 31141 and sliding connected to the third guide groove 31151, that is, the first moving end 31191 is slidably connected to both the first guide groove 31141 and the third guide groove, such that the first moving end 31191 can be moved to any preset position by the cooperation of the first guide groove 31141 and the third guide groove 31151 by moving the second guide body 3115 relative to the first guide body. Similarly, the other end of the second moving end 31161 is passing through the second guide groove 31142 and slidably connected to the third guide groove 31151, that is, the second moving end 31161 is slidably connected to both the second guide groove 31142 and the third guide groove 31151, such that the second moving end 31161 can be moved to any preset position by the cooperation of the second guide groove 31142 and the third guide groove 31151 by moving the second guide body 3115 relative to the first guide body.

In some embodiments, the second guide body 3115 is provided with a guide rack 31152.

Optionally, the second body 3120 further includes a fourth gear 3117 for moving the second guide body 3115 and a second switch member 3118 for controlling rotation of the fourth gear 3117, wherein the second switch member 3118 is partially or entirely located outside the second body 3120, and the second switch member 3118 may include a rotating shaft and a rotating block, wherein the rotating block is located outside the second body 3120, and one end of the rotating shaft is connected to the rotating block and the other end is connected to the fourth gear 3117. The fourth gear 3117, which is in transmission connection with the guide rack 31152, rotates to drive the second guide body 3115 to move relatively to the first guide body, so as to drive the first moving end 31191 and the second moving end 31161 to move along the first guide groove 31141 and the second guide groove 31142 respectively. It should be appreciated that the structure for driving the second guide body is not limited to the above-described embodiment, and a driving motor or other devices and structures may be provided in the second body 3120 to drive the second guide body to move.

It should be appreciated that the second guide body can be any structure besides the above-mentioned structure, as long as the first moving end 31191 and the second moving end 31161 can be driven to move along the first guide groove 31141 and the second guide groove 31142 respectively, for example, the first moving end 31191 and the second moving end 31161 can be driven to move by a dual motor or a dual cylinder.

Similarly, the second assembly 3112 can also be rotated in the above manner, and the disclosure is not set forth herein. In some embodiments, the shapes of the first guide groove 31141 and the second guide groove 31142 can be adjusted according to actual needs, so as to change the moving tracks of the first assembly 3111 and the second assembly 3112, and the disclosure is not limited in particular.

It should be appreciated that the first connection bar 31192 and the second connection bar 31162 are made of rigid material.

Figure 48:
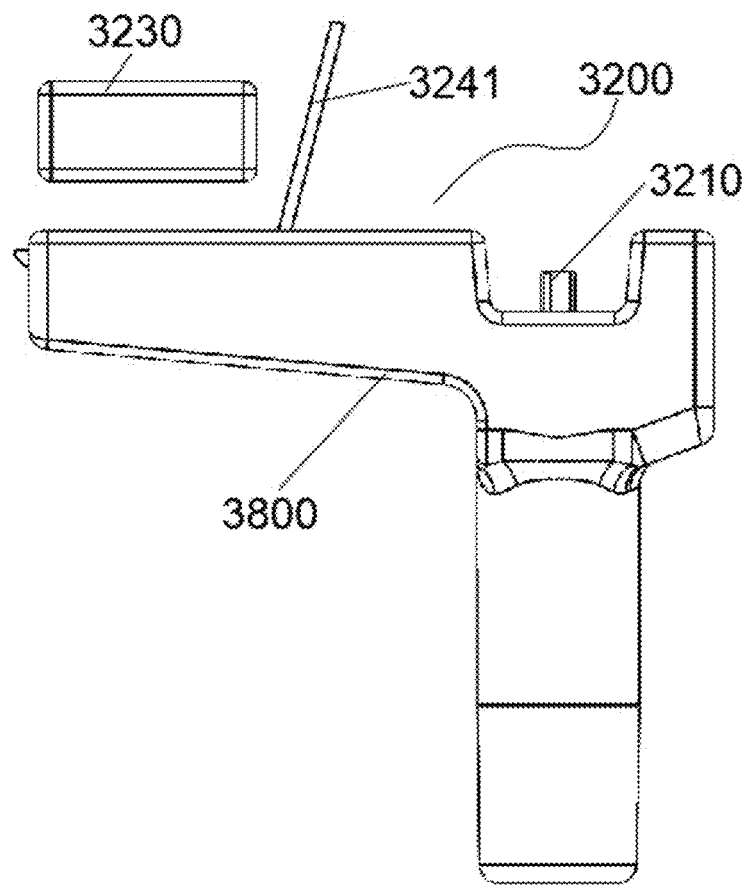
FIG. 48 is a schematic view of a power assembly (including a protective cover) according to an exemplary embodiment.
Figure 49:
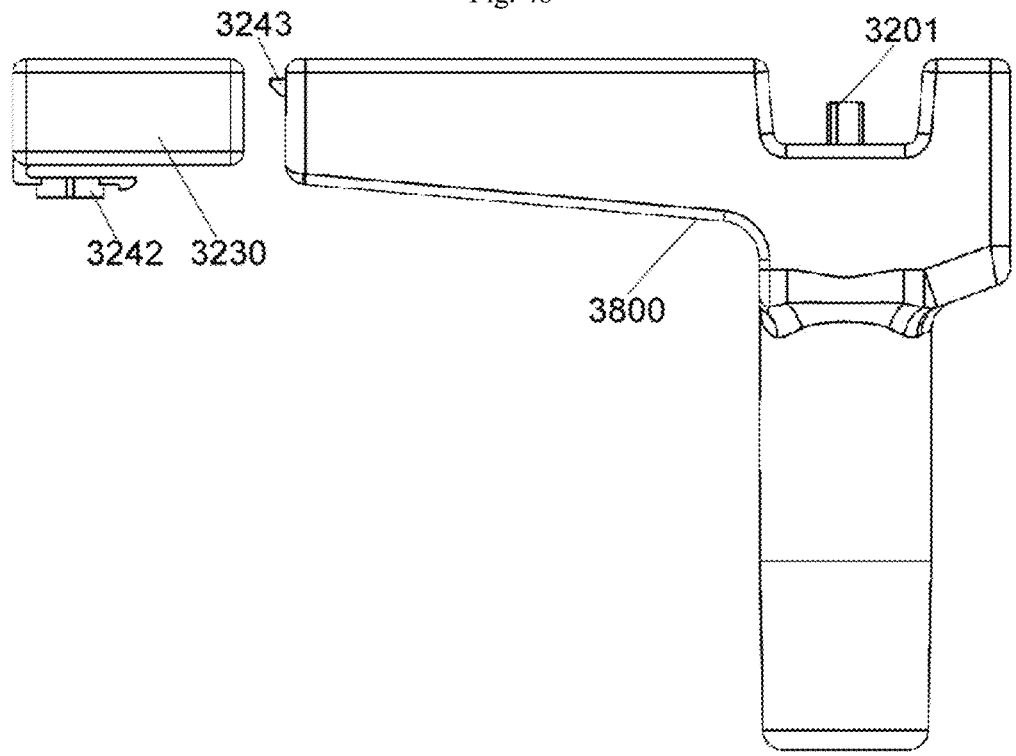
FIG. 49 is a schematic view of the power assembly according to an exemplary embodiment.

In some embodiments, as shown in FIG. 48, the power assembly 3200 includes a first outer shell 3800, a driving device 3201 and a power supply 3230, wherein the first outer shell 3800 is provided with a cavity for accommodating the driving device 3201 and the power supply 3230, and the driving device 3201 may be a motor, a cylinder, preferably a rotating motor and a rotating cylinder. The power supply 3230 can be an external power supply or a battery. In some embodiments, the first outer shell 3800 is provided with a battery compartment for accommodating the battery, the battery compartment may include electrical contacts, an inductive connecting feature, a capacitive connecting feature, and/or any other suitable type of features capable of delivering power to a control module. The power supply 3230 may include a pack of one or more nickel-metal hydride batteries, lithium batteries, such as prismatic lithium ion batteries, nickel cadmium batteries, or any other type of portable power supply. Batteries are classified as being rechargeable multiple times and/or disposable non-rechargeable. If the battery is designed to be used for multiple times, the rechargeable socket is provided on the battery compartment, and if the battery is designed to be disposable, the used battery is disassembled and discarded after each operation, and a new battery is reassembled before the next operation.

The power assembly 3200 is a reusable assembly that requires cleaning and sterilization prior to each operation. To ensure that product function is not affected after sterilization, the housing of the power assembly 3200 is designed to be hermetically sealed to prevent substances entering the interior of the power assembly 3200 during the sterilization process.

In some embodiments, the battery compartment is provided with a protective cover 3241, as shown in FIG. 48. When the battery is installed, the protective cover 3241 is opened, the battery (in this embodiment, the power supply 3230 is a built-in battery) is disposed in the battery compartment, and the protective cover 3241 is covered. The battery can be disassembled in the same way.

In some embodiments, a battery power supply (in this embodiment, the power supply 3230 is a battery) is provided with a third fixing member 3242, and a first outer shell 3800 is provided with a matched fourth fixing member 3243, and the battery is detachably mounted on the first outer shell 3800 through the third fixing member 3242 and the fourth fixing member 3243; the third fixing member 3242 and the fourth fixing member 3243 may be matched snap structures, bolt structures or magnetic connection structures. In some embodiments, the third fixing member 3242 is a lock and the fourth fixing member 3243 is a clip; the battery is pushed by the user to the bottom of the battery compartment during installation, such that the third fixing member 3242 and the fourth fixing member 3243 are locked to each other.

In some embodiments, the surgical instrument 1 further includes a second central processing unit 3203 in signal connection with the first central processing unit 3700. The second central processing unit 3203 may be provided separately from the first central processing unit 3700 or may be integrally formed with the first central processing unit 3700, as the case requires. The second central processing unit 3203 may include a microprocessor, an application specific integrated circuit (ASIC), a memory, a printed circuit board (PCB), a storage device (such as a solid state drive or hard disk), firmware, software, and/or various other suitable components. The first central processing unit 3700 is operable to receive inputs from the end transmission assembly, the sensors, the operating mechanism, and to drive the motor based on one or more control algorithms and based on inputs received from the sensors or the operating mechanism. The first central processing unit 3700 may include a microprocessor, an application specific integrated circuit (ASIC), a memory, a printed circuit board (PCB), a storage device (such as a solid state drive or hard disk), firmware, software, and/or various other suitable components.

In some embodiments, the second central processing unit 3203 also includes a tissue identification module (such as a current detection device). The specific detection process is as follows: when the tissue is clamped by the jaws, the clamping force varies due to different tissue types and tissue thicknesses, and the tissue load can be determined through the feedback of the motor current. The second central processing unit 3203 then adjusts firing speed and firing force according to the tissue load. If the tissue is determined to be thick, the firing button is continuously closed, the scalpel holder moves forward at a low speed, and the motor provides a larger firing force to ensure the cutting effect; on the contrary, if the tissue is determined to be thin, the firing button is closed, the scalpel holder moves forwards at a high speed, and the motor provides small firing force to ensure the cutting efficiency.

The central processing unit 3203 further includes an intelligent hibernation module, wherein the intelligent hibernation module is used to stop the power assembly 3200 from operating. A specific embodiment is as follows: when the system counts down, the system enters a hibernation mode, in which the indicator light is not on and the motor cannot be driven, such that the minimum energy consumption system is ensured to the utmost extent. A wake-up mode can be activated by pressing the key, such that all functions of the stapler can be normally used. It can be identified by hand touch of an induction capacitor, to switch the hibernation mode and the wake-up mode. Or, a membrane switch is used to switch the hibernation mode and the wake-up mode. The intelligent hibernation module may be implemented by a timer.

The surgical instrument 1 further includes a wireless communication device, which is in signal connection with the second central processing unit. The wireless communication device may be provided using the Bluetooth protocol, Zigbee protocol, other protocols, or even other modalities (such as non-RF wireless communication). Users can also adopt electrical contact connections for communication. Such communication can be used in between the first body 3110 and the power assembly 3200, or between the power assembly 3200 and the second body 3120 for transmitting data.

In the description of the present disclosure, it should be noted that the terms "center", "upper", "lower", "left", "right", "vertical", "horizontal", "inner", "outer", and the like indicate orientations or positional relationships based on orientations or positional relationships shown in the drawings, only for convenience of description and simplification of description, but do not indicate or imply that the device or element referred to must have a particular orientation, be constructed in a particular orientation, and operate, and thus, should not be construed as limiting the present disclosure. Furthermore, the terms "first," "second," and "third" are used for descriptive purposes only and are not to be construed as indicating or implying relative importance.

In the description of the present disclosure, it should be noted that, unless explicitly stated or limited otherwise, the terms "connect" and "connected" are to be interpreted broadly, e.g., as being fixed or detachable or integrally connected; can be mechanically or electrically connected; they may be connected directly or indirectly through an intervening medium, or they may be interconnected between two elements. The term "communicate" is also to be appreciated broadly, i.e., may be direct or indirect via the intervening medium. The specific meaning of the above terms in the present disclosure can be appreciated in a specific case to those of ordinary skill in the art.

In addition, technical features involved in different embodiments of the present disclosure described below may be combined with each other as long as they do not conflict with each other.

As used in this disclosure and the appended claims, the singular forms "a", "an", and "the" are intended to include the plural forms as well, unless the context clearly indicates otherwise. It should also be appreciated that the term "and/or" as used herein refers to and encompasses any and all possible combinations of one or more of the associated listed items.

The term "plurality" in the present disclosure and appended claims refers to two or more than two unless otherwise indicated.

The terms "proximal (proximal end) and" distal (distal end) are relative to a clinician manipulating the handle of the surgical instrument 1, wherein "proximal (proximal) refers to a portion closer to the clinician and" distal (distal) refers to a portion further from the clinician.

It will be apparent to those skilled in the art that various changes and modifications can be made in the disclosure without departing from the spirit and scope of the disclosure. Thus, it is intended that the present disclosure also encompass such modifications and variations as fall within the scope of the claims and their equivalents.

What is claimed is:

1. A control end of a surgical instrument, comprising a housing, a power assembly and a transmission assembly, wherein the housing comprises a first body and a second body, a first cavity for accommodating the power assembly is arranged between the first body and the second body, the power assembly is detachably arranged in the first cavity, a connector is provided between the power assembly and the transmission assembly; the transmission assembly comprises a gear set and a screw, or a gear set and a rack, wherein the power assembly is in transmission connection with the gear set via the connector, and the gear set is in transmission connection with the screw or the rack; and wherein
the first cavity is closed when the first body and the second body are in a first state; and
the first cavity is open when the first body and the second body are in a second state.

2. The control end according to claim 1, wherein the power assembly is connected to the transmission assembly through the connector in the first cavity to drive the transmission assembly to move.

3. The control end according to claim 2, wherein an input end of the transmission assembly is provided with a fixing hole, and the input end of the transmission assembly is in transmission connection with an end of the connector through the fixing hole; a first resetting spring is disposed in the fixing hole, an end of the first resetting spring is abutted against an end of the connector, another end of the first resetting spring is abutted against the fixing hole; and another end of the connector can be in transmission connection with the power assembly.

4. The control end of claim 2, wherein the power assembly outputs power to the gear set to drive the screw or the rack to move linearly.

5. The control end according to claim 4, wherein the control end is provided with a rotation mechanism for rotating an end effector, wherein the second body comprises a rotating lock apparatus, and the rotation mechanism is locked through the rotating lock apparatus; the screw or the rack is provided with a ganged portion, and the rotating lock apparatus is provided with a firing lock portion, wherein the screw or the rack actuates the rotating lock apparatus through a cooperation of the ganged portion and the firing lock portion to unlock the rotation mechanism.

6. The control end according to claim 4, further comprising a resetting mechanism, wherein the rack or the screw is moved by actuating of the resetting mechanism.

7. The control end according to claim 1, wherein the first body is detachably connected to the second body.

8. A surgical instrument, comprising an end effector and the control end of claim 1, wherein the end effector is detachably connected to the second body.

9. A control end of a surgical instrument, comprising a housing and a power assembly, wherein the housing comprises a first body and a second body, a first cavity for accommodating the power assembly is arranged between the first body and the second body, and the power assembly is detachably arranged in the first cavity, wherein
the first cavity is closed when the first body and the second body are in a first state,
the first cavity is open when the first body and the second body are in a second state, and wherein the first body is provided with a snap portion, and the second body is provided with a connection body slidably disposed on the second body; the connection body is provided with a snap connection portion in connection with the snap portion, and the snap connection portion is connected to or separated from the snap portion by sliding the connection body.

10. The control end according to claim 9, wherein the snap connection portion comprises a guide inclined surface and the snap portion comprises a guide inclined surface, and the first body or the second body is provided with a first opening; wherein the connection body is actuated to slide by cooperation of the guide inclined surface of the snap connection portion and the guide inclined surface of the snap portion when the first body and the second body are getting close to each other, such that the snap connection portion is capable of entering the first body through the first opening, or such that the snap portion is capable of entering the second body through the first opening.

11. The control end according to claim 10, wherein the snap portion comprises a limiting groove disposed in the first body, the limiting groove is provided with a first guide portion, the first guide portion includes the guide inclined surface of the snap portion; the first opening is arranged on the limiting groove, and the first guide portion is arranged at the first opening and partially blocks the first opening; the snap connection portion is provided with a second guide portion matched with the first guide portion, and the second guide portion includes the guide inclined surface of the snap connection portion; wherein the snap connection portion is driven to slide to the first opening and enter the limiting groove through the first opening via the cooperation of the guide inclined surface of the first guide portion and the guide inclined surface of the second guide portion when the snap connection portion is getting close to the first guide portion along a first direction.

12. The control end according to claim 9, wherein the snap portion comprises a limiting groove disposed in the first body, the snap connection portion is capable of moving along the limiting groove between an engaged position and a disengaged position; wherein the snap portion is in snap connection with the snap connection portion when the snap connection portion is in the engaged position, and wherein the snap portion and the snap connection portion are separated from each other when the snap connection portion is in the disengaged position.

13. The control end according to claim 12, wherein the second body is provided with a second resetting spring for driving the snap connection portion to return to the snap connection position when the snap connection portion is located in the limiting groove.

14. The control end according to claim 9, wherein the control end is provided with a rotation mechanism, the second body comprises a rotating lock apparatus, the rotation mechanism is locked through the rotating lock apparatus.

15. The control end according to claim 14, wherein the rotating lock apparatus is provided with a disassembling lock portion, and the connection body is provided with a disassembling protrusion portion; wherein the connection body actuates the rotating lock apparatus to unlock the rotation mechanism by cooperation of the disassembling protrusion portion and the disassembling lock portion.

16. The control end according to claim 15, wherein the second body is provided with a first actuating mechanism for actuating the connection body.

17. A control end of a surgical instrument, comprising a housing and a power assembly, wherein the housing comprises a first body and a second body, a first cavity for accommodating the power assembly is arranged between the first body and the second body, and the power assembly is detachably arranged in the first cavity, wherein
  the first cavity is closed when the first body and the second body are in a first state,
  the first cavity is open when the first body and the second body are in a second state,
  and wherein the first body is movably connected to the second body, such that the first body and the second body are switchable between the first state and the second state.

18. The control end according to claim 17, wherein the first body comprises a first assembly, a second assembly, and a guide structure; the first assembly and the second assembly cooperate with the guide structure such that the first assembly and the second assembly are open and closed, wherein the first assembly and the second assembly cooperate with the second body to form the first cavity when the first assembly and the second assembly are closed.

19. The control end according to claim 18, wherein the guide structure is provided with a first guide groove and a second guide groove, wherein the first assembly is provided with a first buckling portion and is slidably connected to the first guide groove through the first buckling portion, and wherein the second assembly is provided with a second buckling portion and is slidably connected to the second guide groove through the second buckling portion.

20. The control end according to claim 19, wherein an end of the first buckling portion is slidably connected to the first guide groove, another end of the first buckling portion is hinged to the first assembly; wherein the second buckling portion comprises a second moving end and a second connection bar, an end of the second moving end is hinged to an end of the second connection bar, another end of the second moving end is slidably mounted to the second guide groove, and another end of the second connection bar is hinged to the first assembly.

* * * * *